United States Patent [19]
Roy

[11] Patent Number: 5,922,315
[45] Date of Patent: Jul. 13, 1999

[54] ADENOVIRUSES HAVING ALTERED HEXON PROTEINS

[75] Inventor: Soumitra Roy, Gaithersburg, Md.

[73] Assignee: Genetic Therapy, Inc., Gaithersburg, Md.

[21] Appl. No.: 08/788,674

[22] Filed: Jan. 24, 1997

[51] Int. Cl.$^6$ .......................... A61K 35/76; A61K 48/00; C12N 7/01; C12N 15/86
[52] U.S. Cl. ................. 424/93.2; 435/235.1; 435/320.1; 435/69.1; 435/456; 435/466; 424/199.1
[58] Field of Search .............................. 424/199.1, 233.1, 424/93.2; 435/235.1, 320.1, 69.1, 456, 466

[56] References Cited

U.S. PATENT DOCUMENTS 5,543,328  8/1996  McClelland et al. .

OTHER PUBLICATIONS

Roy et al (Journal of Virology 72:6875–6879, 1998.
Mastrangeli et al. Pediatrics Pulmonology, Supplement 12, p. 230, abstract 180, Sep. 1995.
Gene, vol. 13, pp. 311–317 (1981) Boursnell et al.
Current Topics in Microbilogy and Immunology, vol. 110, pp. 191–220 (1984) Wadell.
Science, vol. 232, pp. 1148–1151 (May 30, 1986) Roberts et al.
Journal of General Virology, vol. 75, pp. 133–139 (1994) Crompton et al.
Virology, vol. 205, pp. 439–452 (1994) Bailey et al.
Gene Therapy, vol. 3, pp. 154–162 (1996) Kass—Eisler et al.
Human Gene Therapy, vol. 7, pp. 79–87 (Jan. 1, 1996) Mastrangeli et al.
Journal of Virology, vol. 70, No. 4, pp. 2116–2123 (Apr. 1996) Gall et al.
Mautner, V. et al. Virology, vol. 131, pp. 1–10, 1983.
Crawford–Mikza, L. et al. Journal of Virology, vol. 70, p. 1836–1844, Mar. 1996.
Mautner, V. et al. Virology, vol. 139, pp. 43–52, 1984.
Pring–Akerblom, P. et al. Virology, vol. 212, pp. 232–236, 1995.
Crawford–Mikzsa, L. et al. Virology, vol. 224, pp. 357–367, 1996.
Verma, I. et al. Nature, vol. 389, Sep. 18, 1997, pp. 239–242.

*Primary Examiner*—Mary E. Mosher
*Attorney, Agent, or Firm*—Elliot M. Olstein; Raymond J. Lillie

[57] ABSTRACT

An adenovirus wherein at least one portion of at least one loop region of the hexon is changed. In one embodiment, the adenovirus, prior to modification, is of a first serotype, and at least a portion of at least one loop region of the hexon is removed and replaced with at least a portion of at least one loop region of the hexon of an adenovirus of a second serotype. Such modified adenoviruses do not have epitopes which are recognized by neutralizing antibodies to the unmodified adenovirus of the first serotype.

10 Claims, 28 Drawing Sheets

FIG. 1Aa

```
  1  MATPSMMPQWSYMHIAGQDASEYLSPG
  1  MATPSNMPQWSYMHISGQDASEYLSPG

51  APTHDVTTDRSQRLTLRFVPVDREDTT
 51  APTHDVTTDRSQRLTLRFIPVDREDTA
               ↑Age I

101  FDIRGVLDRGPSFKPYSGTAYNSLAPK
101  FDIRGVLDRGPTFKPYSGTAYNALAPK

140  ------------KLNTFAQAPYLSD
151  DDNEDEVDEQAEQQKTHVFGQAPYSGI

176  NKTYQPEPQVGPSEWNTSIENVKAGGR
197  DKTFQPEPQIGESQWYET-EINHAAGR

226  GQSK-------DDNIELKFFDSANN
246  GQGILVKQQNGKLESQVEMQFFSTTEA  L1

262  PDTHLVFKPTVTNGTIASESLLGQQAA
296  PDTHISYMPTIKEGN--SRELMGQQSM

312  NMGVLAGQASQLNAVVDLQDRNTELSY
344  NMGVLAGQASQLNAVVDLQDRNTELSY
                        →L 2

362  YDPDVRVIENHGVEDELPNYCFPLSAV
394  YDPDVRIIENHGTEDELPNYCFPLGGV
```

FIG. IAb

```
L V Q F A R A T D T Y F T L G N K F R N P T V    AD12.PRO
L V Q F A R A T E T Y F S L N N K F R N P T V    AD5.PRO

Y S Y K A R F T L A V G D N R V L D M A S S Y    AD12.PRO
Y S Y K A R F T L A V G D N R V L D M A S T Y    AD5.PRO
                              ↑L1
G A P N A S Q W S D N A - - - - - - - - - -      AD12.PRO
G A P N P C E W D E A A T A L E I N L E E D      AD5.PRO

T I T A A D G I K V G T D T A Q A G A A V Y A    AD12.PRO
N I T K - E G I Q I G V E G Q - - - T P K Y A    AD5.PRO

A L K Q T T A M Q P C Y G S Y A R P T N E H G    AD12.PRO
V L K K T T P M K P C Y G S Y A K P T N E N G    AD5.PRO

A A N - - - - - T A Q V V F Y T E D V N L E M    AD12.PRO
T A G N G D N L T P K V V L Y S E D V D I E T    AD5.PRO
                              BsrGI
P N R A N Y I A F R D N F I G L M Y Y N S T G    AD12.PRO
P N R P N Y I A F R D N F I G L M Y Y N S T G    AD5.PRO

Q L M L D A L G D R T R Y F S L W N S A V D S    AD12.PRO
Q L L L D S I G D R T R Y F S M W N Q A V D S    AD5.PRO

G E I K N Y K G I K P D N G G G G W T A D N      AD12.PRO
I N T E T L T K V K P K T G Q E N G W E K D A    AD5.PRO
```

FIG. 1Ac

```
412  T-vSEANHIGNIAMEINLQANLWR
444  TEFSDKNEIRVGNNFAMEINLNANLWR
                          ↓L2
461  LPDNKNTYEYMNGRVTAPGLVDTYVNI
494  ISDNPNTYDYMNKRVVAPGLVDCYINL

511  RYRSMLLGNGRFVPFHIQVPQKFFAIR
544  RYRSMLLGNGRYVPFHIQVPQKFFAIK

561  QSTLGNDLRVDGASVRFDNIALYANFF
594  QSSLGNDLRVDGASIKFDSICLYATFF

611  NDYLCAANMLYPIPANATSVPISIPSR
644  NDYLSAANMLYPIPANATNVPISIPSR

661  GFDPYSVYSGTIPYLVGTFYLNHTFKK
694  GYDPYYTYSGSIPYLDGTFYLNHTFKK
          ↑L4
711  EIKRSVDGEGYNVAQCNMTKDWFLIQM
744  EIKRFVDGEGYNVAQCNMTKDWFLVQM

761  FFRNFQPMSRQVVDTTEYKNYKKVTVE
794  FFRNFQPMSRQVVDDTKYKDYQQVGIL
                    ↓L4
811  ANYPYPLIGQTAVESITQKKFLCDRVM
844  ANFPYPLIGKTAVDSITQKKFLCDRTL
```

FIG. IAd

```
S F L Y S N V G L Y L P D D L K Y T P G N I K   AD12.PRO
N F L Y S N I A L Y L P D D K L K Y S P S N V K  AD5.PRO

G A R W S P D V M D N V N P F N H H R N A G L   AD12.PRO
G A R W S L D Y M D N V N P F N H H R N A G L   AD5.PRO

N L L L P G S Y T Y E W N F R K D V N M I L     AD12.PRO
N L L L P G S Y T Y E W N F R K D V N M V L     AD5.PRO

P M A H N T A S T L E A M L R N D T N D Q S F   AD12.PRO
P M A H N T A S T L E A M L R N D T N D Q S F   AD5.PRO

N W A A F R G W S F T R L K T K E T P S L G S   AD12.PRO
N W A A F R G W A F T R L K T K E T P S L G S   AD5.PRO

V S I M F D S S V S W P G N D R L L T P N E F   AD12.PRO
V A I T F D S S V S W P G N D R L L T P N E F   AD5.PRO

L S H Y N I G Y Q G F Y I P E S Y K D R M Y S   AD12.PRO
L A N Y N I G Y Q G F Y I P E S Y K D R M Y S   AD5.PRO

F Q H N S G F V G Y L G P T M R E G Q A Y P     AD12.PRO
H Q H N S G F V G Y L A P T M R E G Q A Y P     AD5.PRO

W R I P F S S N F M S M G A L T D L G Q N M L   AD12.PRO
W R I P F S S N F M S M G A L T D L G Q N L L   AD5.PRO
```

FIG. 1Ae

```
861  Y A N S A H A L D M T F E V D P M D E P T L L Y V L F
894  Y A N S A H A L D M T F E V D P M D E P T L L Y V L F
                                    ↑ BamHI

```
E V F D V V R I H Q P H R G V I E A V Y L R T    AD12.PRO
E V F D V V R V H R P H R G V I E T V Y L R T    AD5.PRO
```

```
                                                 AD12.PRO
                                                 AD5.PRO
```

FIG. 1Bb

```
G T G G T C T T A C A T G C A C A T C G C C G G  AD12.SEQ
G T G G T C T T A C A T G C A C A T C T C G G G  AD5.SEQ

C C G G T C T G T G G T G C A A T T C G C C C G  AD12.SEQ
C C G G G C T G G T G G C A G T T T G C C C C G  AD5.SEQ

A A C A A G T T T A G A A A C C C C A C C G T G  AD12.SEQ
A A C A A G T T T A G A A A C C C C A C G G T G  AD5.SEQ
              ← SZR46 →

T C G C T C G C A G C G T C T G A C G C T G C G  AD12.SEQ
C C G G T C C C A G C G T T T G A C G C T G C G  AD5.SEQ
     AgeI

C T A C C T C T T A C T C C T T A C A A G G C T  AD12.SEQ
C T G C G T A C T C G T C G T A C A A A G G C G  AD5.SEQ

G T G T T T A G A C A T G G C T A G T T C T T A C  AD12.SEQ
G T G C T G G A C A T G G A C T T C C A C G T A C  AD5.SEQ
```

```
TGGTCCCAGTTTTAAGCCCTATTC  AD12.SEQ
GGGCCCTACTTTTAAGCCCTACTC  AD5.SEQ

CAAAGGCGGCTCCTAATGCTTCAC  AD12.SEQ
CCAAGGGTGCCCCAAATCCTTGCG  AD5.SEQ

---AATA--CCT------------  AD12.SEQ
GAATAAACCTAGAAGAAGAGGAC   AD5.SEQ

GCGA--------------------CA  AD12.SEQ
GCAAGCTGAGCAGCAAAAAACTCA   AD5.SEQ

GTATTAAGTTGGAACAGACACCG   AD12.SEQ
GTATAAATATTACAAAGGAGGGTA  AD5.SEQ

-----GTATGCCAACAAAACTTAT  AD12.SEQ
CCTAAATATGCCGATAAAACATTT  AD5.SEQ

TGAATGGAACACCAGCATTGAAA   AD12.SEQ
TCAGTGGTA---CGAAACTGAAAT  AD5.SEQ

AGCAAACACTGCAATGCAGCCGT   AD12.SEQ
AAAGACTACCCCAATGAAACCAT   AD5.SEQ

AACGAACACGGAGGACAATCCA-   AD12.SEQ
AATGAAAATGGAGGGCAATGCATT  AD5.SEQ
```

```
AD12.SEQ  T - A A G T T C - - - - - - - T T
AD5.SEQ   A G A A A G T C A A G T G G A A A T G C A A T T
                    →SZR57 (COMPLEMENT)

AD12.SEQ  A C A C T G - - - - - - - C T C - - -
AD5.SEQ   G C A A T G G T G A T A A C T T G A C T C C T A

AD12.SEQ  A A C C T T G A A A T G C C A G A C A C G C A T
AD5.SEQ   G A T A T A G A A A A C C C C A G A C A C T C A T

AD12.SEQ  T G G A A C A A T T G C T T C T G A G T C G C T
AD5.SEQ   - A G A A G G T A A C T C A C G A G A - A C T

AD12.SEQ  G A G C A A A C T A C A G G C A T T C A G A G
AD5.SEQ   G G C C T A A T T T A C A T T T C T T T T A G G G

AD12.SEQ  A A C A G T A C A G C C T G C A A G A C T G G T G T A
AD5.SEQ   A A C A C G G G T A A T A T G G G T G T T

AD12.SEQ  C G C A G T A G A C C T T T G G A G A C A G A C A G
AD5.SEQ   T G C T G T T G T A G A T T T G C A A G A C A G

AD12.SEQ  T G C T G G A T G C T T C C A T T G G A G A C A G A A
AD5.SEQ   T G C T T G A T T C C A T T G G T G A T A G A A

AD12.SEQ  G C A G T G G A C A G T T A C G A C C C T G A C
AD5.SEQ   G C T G T T G A C A G C T A T G A T C C A G A T
```

FIG. 1B9

```
1096 GTTCGTTATTGAGAATCACGGGT
1192 GTTAGAATTATTGAAAATCATGGAAC

1146 CTTCCTCTTAGCGCAGTAGGTGAAA
1242 CTTTCCACTGGGAGGTGATTAATA

1190 TTAAGCCAGATAACGAGGAGGAGGT
1292 CTAAAACAGGTCAGGAAAATGGATGG

1240 AGTGAAGCAAACCACATAGGCATTGG
1341 AGATAA--AAATGAAATAAGAGTTGG

1290 TTTGCAGGCTAATTGTGGAGAAGCT
1389 TCTAAATGCCAACCTAAAGTACAGT

1340 ACCTACCAGACGACTTAAATACACT
1439 ATTTGCCCGACAAGCTACACATGAA

1390 AACAAGAACACCTACGAGTACATGAA
1489 ACCCAAACACCACCTAAAGTACATGAA

1440 GGTGGATACCTATGTCAATATCGGCG
1539 AGTGGACTGCTACATTAACCTTGGAG

1490 ATAATGTAAACCCTTTTAACCACCAC
1589 ACAAGTCAACCCCATTTAACCACCAC
```

FIG. 1Bh

```
AGAGGATGAACTACCAAATTATTG  AD12.SEQ
TGAAGATGAACTTCCAAATTACTG  AD5.SEQ

TAAAAAT--TACAAAGGCA----   AD12.SEQ
CAGAGACTCTTACCAAGGTAAAAC  AD5.SEQ

GCTGGACTGCCGACACACTGTC    AD12.SEQ
GAAAAGATGCT-ACAGAATTTTC   AD5.SEQ

GAATATAGCCCGCCATGGAAATTAA AD12.SEQ
AATAATTTTTGCCATGGAAATCAA  AD5.SEQ

TCTTGTACTCAAATGTGGCTTAT   AD12.SEQ
TCCTGTACTCCAACATAGCGCTGT  AD5.SEQ

CCAGGAAACACTGTGACTGCCTGAT AD12.SEQ
CCTTCCAACGTAAAAATTTCTGAT  AD5.SEQ

CGGGCGTGTCCCCAGATGCCTGTT  AD12.SEQ
CAAGCGGGGTCCCTTGACCCGGTT  AD5.SEQ

CTTCGCTGGCAGCAGATGTGATGG  AD12.SEQ
CACGCTGGTCCCTTGACTATATGG  AD5.SEQ

CGAAACGCAGGGTTGCGCTACAGA  AD12.SEQ
CGCAATGCCTGGCCTGCGCTACCGC AD5.SEQ
```

FIG. 1Bj

```
1540 TCCATGTTGCTAGGCAATGGGAGATT
1639 TCAATGTTGCTGGGCAATGGTCGCTA

1590 GCAAAATTTTTGCCATCAGAAATT
1689 TCAGAAGTTCTTTGCCATTAAAACC

1640 CTTACGAATGGAACTTTAGAAAGGAT
1739 CTACGAGTGGGAACTTCAGGAAGGAT

1690 CTGGGAAATGATCTTCGGGTGGACGG
1789 CTAGGAAAATGACCTAACGGTTGACGG

1740 TGCCCTGTATGCTAACTTTTTCCCA
1839 TTGCCTTTACGCCAACCTTCTTCCCC

1790 TAGAAGCCATGTTAAGAAATGACACC
1889 TTGAGGCCATGCTTAGAAACGACACC

1840 TTGTGCTGCAAACTTCCTTCGCGAATT
1939 CTCTCCCCAACATGCCTCTACCC

1890 GCCCATTTCAATACCCTTCCCGCAACT
1989 GCCCATCCATCCCCATCCCCGCAACT

1940 TTACTCGCCTAAAACTAAAGAAACT
2039 TCACGCGCCTTAAGACTAAGGAAACC
```

```
1990  CCCTACTTTGTATACTCTGGAACCAT
2089  CCTATTACACCTACTCTGGCTCTAT

2040  CCTAACCACACTTTAAGAAGGTGT
2139  CCTCCAACCACACCTTTAAGAAGGTGG

2090  GTTGGCCCTGGAATGACCGTTTGCTA
2189  GCTGGCCCTGGCAATGACCGCCTGCTT

2140  CGTTCTGTGGAGGGGATACAA
2239  CGCTCAGTTGACGGGAGGGTTACAA

2190  GGATTGGTTCCTAATACAAATGCTTA
2289  AGACTGGTTCCTGGACAAATGCTAG

2240  GTTTTACATTCCAGAGAGCTACAAG
2339  GCTTCTATATCCCAGAGAGCTACAAG

2290  AACTTTCAGCCCATGAGTAGGCAAGT
2389  AACTTCCAGCCCATGAGCCGTCAGGT

2340  CTACAAAAGTAACCGTAGAGTTTC
2439  CTACCAAGGTGGGCATCCTACACC

2390  GATACCTGGCCCACTATGCGGAG
2489  GCTACCTTGCCCCCACCACTGCGCGAA
```

FIG. 1Bm

```
TCCTATTTAGACGGCACCTTTTA   AD12.SEQ
ACCCTACCTAGATGGAACCTTTA   AD5.SEQ

CAATCATGTTTGACTCCTCCGTGA  AD12.SEQ
CCATTACCTTTGACCTTCTGTCA   AD5.SEQ

ACCCCAAATGAATTTGAAATAAAG  AD12.SEQ
CCCCCAACGAGTTTGAAATTAAG   AD5.SEQ

TGTGGCCCAATGCAATGACTAAA   AD12.SEQ
CGTTGCCCAGTGTAACATGACCAA  AD5.SEQ

GTCATTACAACATTGGATACCAAG  AD12.SEQ
CTAACTACAAACATTGGCTACCAGG AD5.SEQ

GACCCGCATGTATTCTTTCTTTTAGA AD12.SEQ
GACCCGCATGTACTCCTTCTTTAGA  AD5.SEQ

TGTGGATACCACAGAATATAAGAA  AD12.SEQ
GGTGGATGATACTAAATACAAGGA  AD5.SEQ

AACAATAACAACTCAGGATTCGTGG AD12.SEQ
ACAACAACAACTCTGGATTTGTTG  AD5.SEQ

GGACAAGCTTACCCCGCAACTAT   AD12.SEQ
GGACAGGCCTACCCCTGCTAACTTC AD5.SEQ
```

FIG. 1Bn

```
2440  CCTACCCTCTTATAGGCCAACAGC
2539  CCCTATCCGCTTATAGGCAAGCGC

2490  GTTTCTTATGCGATCGTGTTATGTGGC
2589  GTTTCTTTGCGATCGCACCCTTTGGC

2540  TGTCTATGGGGGCGCTAACGGATCTT
2639  TGTCTATGTGCGCACTCACAGACCT G

2590  TCAGCCCATGCTCTAGACATGACATT
2689  TCGCCCACGCGCTAGACATGACTTT

2640  TACCCTCCTTATGTTTATTTGAAG
2739  CACCCTTCTTTATGTTTTTGTTTGAAG

2690  AGCCACCCGGCGCGGTCATTGAAGCG
2789  GCCGCACCCGGCGCGGTCATCGAAACC

2740  GCGGGTAACGCTACCACCTAA
2839  GCCGGCAACGCCACACAATA
```

FIG. 1Bo

```
AD12: T GT G G A A A G C A T C A C A G A A A A A   AD12.SEQ
AD5:  A G T T G A C A G C A T T A C C C A G A A A A A   AD5.SEQ

AD12: G C A T C C C A T T T T C T T A G T A A C T T C A   AD12.SEQ
AD5:  G C A T C C C A T T C T C C C A G T A A C T T T A   AD5.SEQ

AD12: G G C A A A A T G C T T G T T A C G C A A A C   AD12.SEQ
AD5:  G G C C A A A A C C T T C T C T A C G C C A A C   AD5.SEQ
              Bam HI

AD12: T G A G G T G G A T C C A A T G G A T G A G C C   AD12.SEQ
AD5:  T G A G G T G G A T C C C A T G G A C G A G C C   AD5.SEQ
                    ← SZR 45 (COMPLEMENT)

AD12: T T T C G A C G T G G T A C G C A T T C A C C   AD12.SEQ
AD5:  T C T T T G A C G T G G T C C G T G T G C A C C   AD5.SEQ

AD12: G T C T A C C T G C G C A C G C C C C T T C T C G   AD12.SEQ
AD5:  G T G T A C C T G C G C A C G C C C C T T C T C G   AD5.SEQ
```

Ad 5 d1327 (34057 bps)

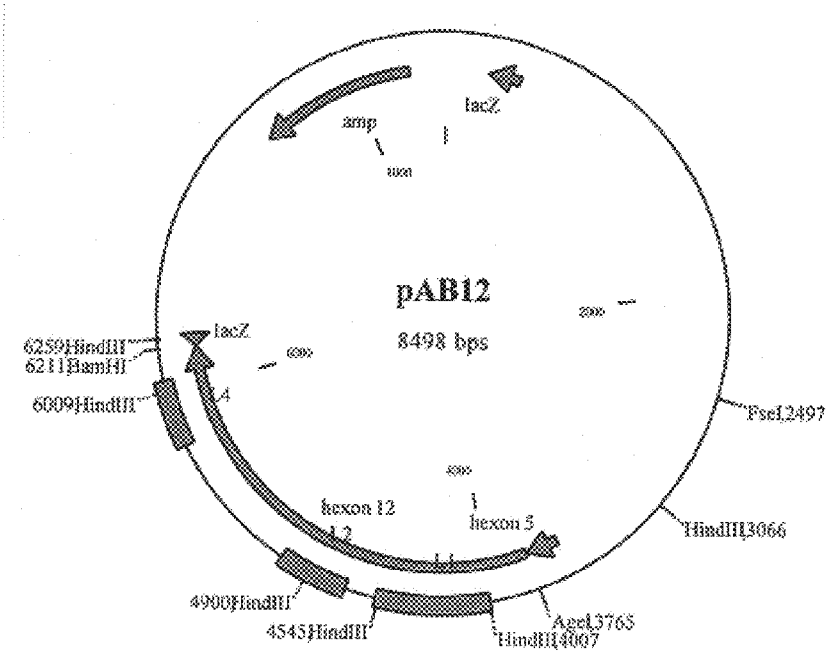
FIG. 4a
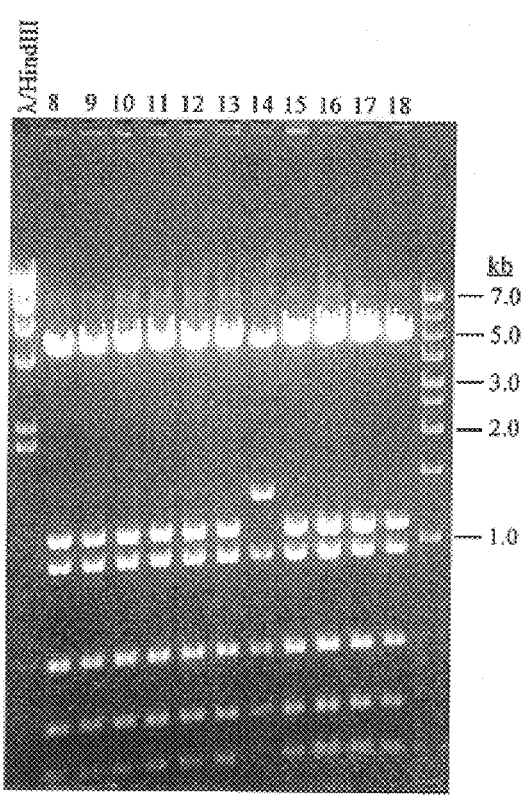

… # ADENOVIRUSES HAVING ALTERED HEXON PROTEINS

This invention relates to adenoviruses which may be employed in gene therapy. More particularly, this invention relates to adenoviruses in which a portion of the hexon protein of the adenovirus is changed. Still more particularly, this invention relates to adenoviruses wherein at least a portion of at least one loop region of the hexon is changed.

BACKGROUND OF THE INVENTION

Adenovirus genomes are linear, double-stranded DNA molecules of approximately 36 kilobase pairs. Each extremity of the viral genome has a short sequence known as the inverted terminal repeat (or ITR), which is necessary for viral replication. The well-characterized molecular genetics of adenovirus render it an advantageous vector for gene transfer. Portions of the viral genome can be substituted with DNA of foreign origin. In addition, recombinant adenoviruses are structurally stable.

Adenoviruses thus may be employed as delivery vehicles for introducing desired polynucleotide sequences into eukaryotic cells, whereby the adenovirus delivers such polynucleotide sequences to eukaryotic cells by binding cellular receptors.

Adenoviral vectors, however, elicit immune responses, and such immune responses correlate with decreased efficiency of gene transfer and expression after repeated administration. (Yei, et al., *Gene Therapy*, Vol. 1, pgs. 192–200 (1994)). It also was found that neutralizing antibodies to adenovirus block successful repeat administration of the adenovirus. (Smith et al., *Nature Genetics*, Vol. 5, pgs. 397–402 (1993); Kozarsky, et al., *J. Biol. Chem.*, Vol. 269, No. 18, pgs. 13695–13702 (May 1994)).

Immunity to adenovirus is type specific (Wadell, "Molecular Epidemiology of Human Adenoviruses," in *Current Topics in Microbiology and Immunology*, Vol. 110, pgs. 191–220 (1984)), and infection with a particular serotype of adenovirus confers immunity only to that serotype. Successful DNA transduction has been demonstrated using sequential administration of different serotypes. (Mastrangeli, et al., *Human Gene Therapy*, Vol. 7, pgs. 79–87 (Jan. 1, 1996)). In Mastrangeli, an immunizing dose of wild-type Adenovirus 5 (subgroup C), Adenovirus 4 (subgroup E), or Adenovirus 30 (subgroup D) was administered intratracheally to rats, followed by an intratracheal administration of a replication-deficient subgroup C-derived recombinant adenovirus. Efficient gene transfer was not achieved in the rats that were given Adenovirus S. In contrast, effective gene transfer was achieved in the rats that were given Adenovirus 4 or Adenovirus 30.

Kass-Eisler, et al., *Gene Therapy*, Vol. 3, pgs. 154–162 (1996) disclose the administration of a vector derived from Adenovirus 5 which includes a chloramphenicol transferase (CAT) gene to one-day-old mice. Sixty days later, the mice received a second dose of the same vector. After the second administration, expression of CAT increased from about 2,900 units at a 57-day time point to about 27,000 units five days after the second administration. Although the expression of CAT increased, increases in the levels of neutralizing antibodies against Adenovirus 5 also were detected. Thus, Kass-Eisler, et al. show that a second injection of adenovirus is possible only if the normal immune response is "circumvented," such as, for example, by administering the first dose to neonatal mice that are incapable of mounting an effective immune response and perhaps become "tolerant" of the injected adenovirus.

SUMMARY OF THE INVENTION

The present invention is directed to adenoviruses having altered antigenic epitopes. More particularly, the present invention is directed to an adenovirus having an altered hexon protein, and still more particularly, the present invention is directed to an adenovirus of a particular serotype wherein at least a portion of at least one of the loop regions of the hexon of such adenovirus is removed and replaced with at least a portion of the loop region(s) of the hexon of an adenovirus of another serotype.

BRIEF DESCRIPTIONS OF THE DRAWINGS

This invention now will be described with respect to the drawings, wherein:

FIG. 1A shows a computer alignment (DNASTAR MegAlign software) of the predicted hexon amino acid sequences based on published nucleotide sequences, of human Adenovirus 12 (shown as AD12.PRO) (Sprengel, et al., *J. Virol.*, Vol. 68, pgs. 379–389 (1994)) and human Adenovirus 5 (shown as AD5.PRO) (Kinloch, et al., *J. Biol. Chem.*, Vol. 259, pgs. 6431–6456 (1984)). Identical or similar (conservative change) amino acids are boxed. The positions of the loop regions L1, L2, and L4 are shown (based on comparison with the sequence of human Adenovirus 2 as published by Roberts, et al., *Science*, Vol. 232, pgs. 1148–1151 (1986). The positions where the restriction enzymes AgeI, BsrGI, and BamHI cut the corresponding nucleotide sequences also are indicated.

FIG. 1B shows a computer alignment (DNASTAR MegAlign software) of the published nucleotide sequences coding for the hexons of human Adenovirus 12 (shown as AD12.SEQ) and human Adenovirus 5 (shown as ADS) Identical nucleotides are boxed. The recognition sequences for the restriction enzymes AgeI, BsrGI, and BamHI are shown. The regions corresponding to the sequences from which the PCR primers used for amplification of the DNA sequences are shown.

FIG. 2 is a map of the genome of the adenovirus Ad dl327 showing the position of the hexon coding region. The positions of the loop regions L1, L2, and L4 are shown. The recognition sites for the restriction enzymes AscI, AgeI, BsrGI, and BamHI (used for hexon DNA cloning constructions) are indicated.

Figure 4B:
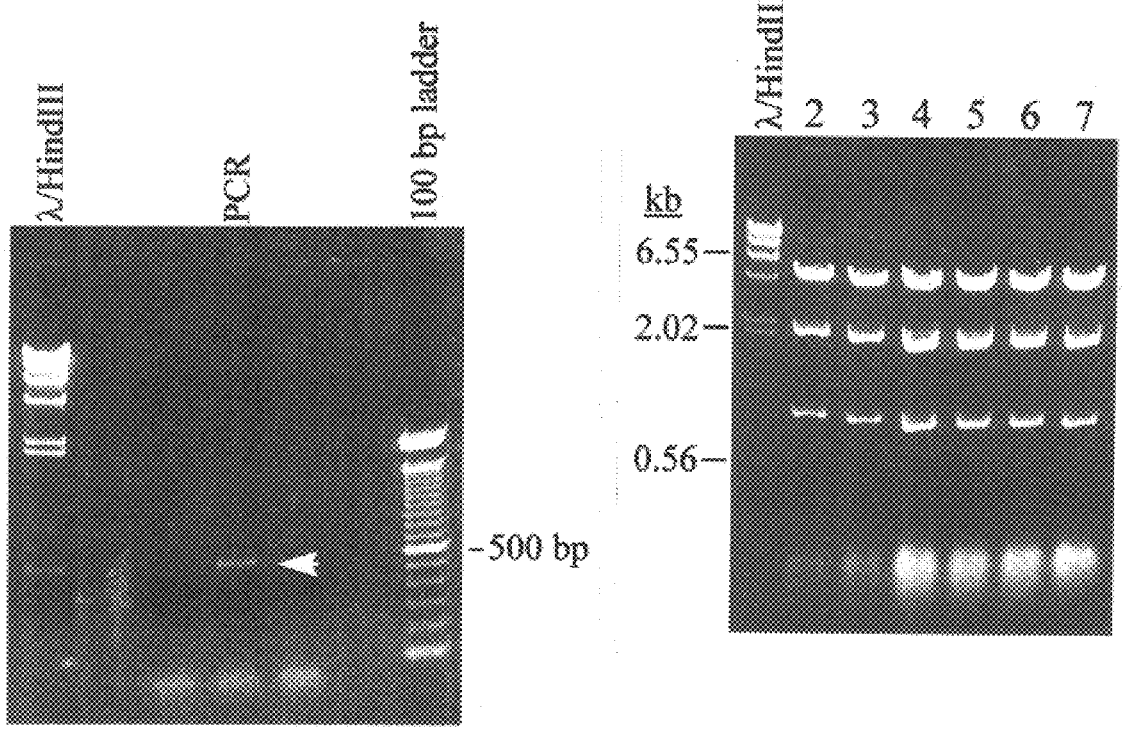
FIG. 4A shows a map of plasmid pABl2, and a gel showing 12 miniprep DNAs digested with HindIII.
Figure 4B:
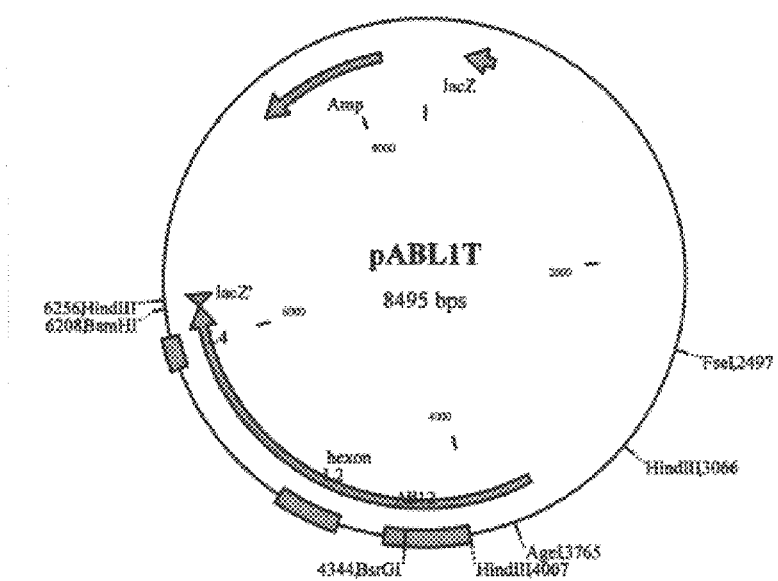

FIG. 4B shows a gel obtained after PCR of the Adenovirus 12 L1 region (upper left), with the arrowhead indicating the position of the PCR product; a gel (upper right) showing putative PABL1T miniprep DNAs cut with HindIII (expected 5,305 and 2,249 and 941 bp bands, lanes 2 to 7 numbered left to right) and a map of plasmid pABL1T.

Figure 5:
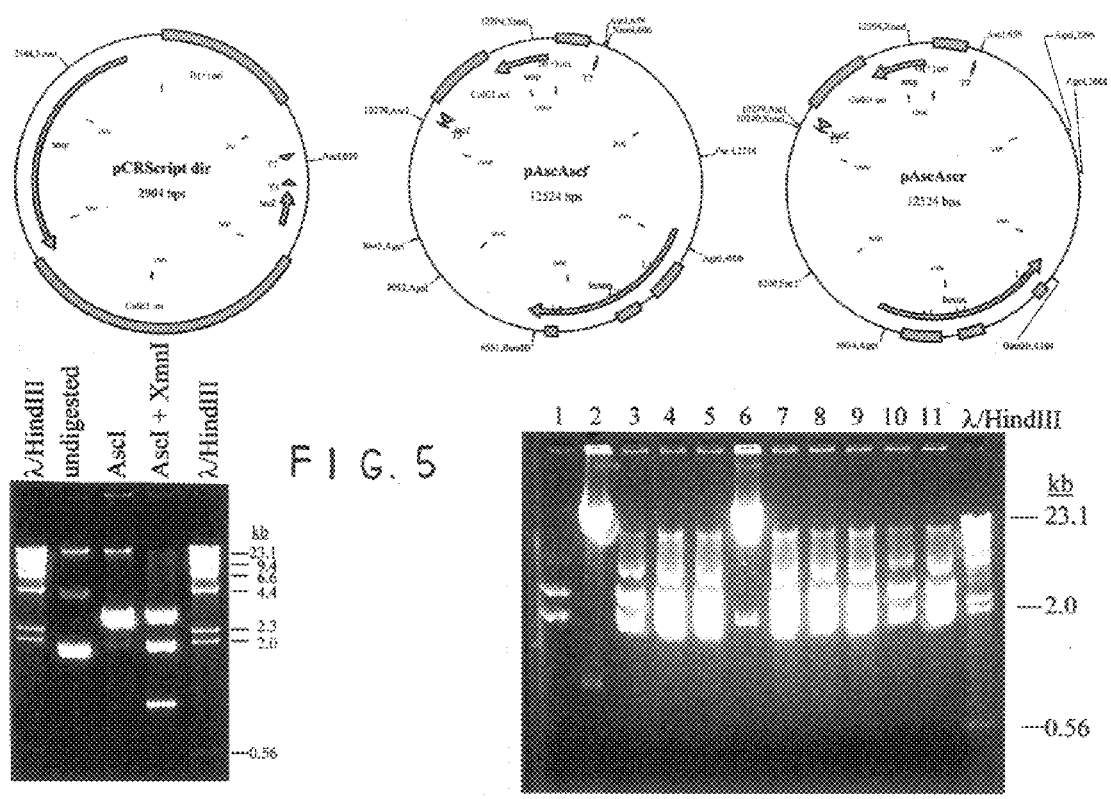

FIG. 5 shows maps of the plasmids pCRScript Direct, pAscAscf, and pAscAscr; a gel showing a diagnostic digest of pCRScript Direct (lower left), and a gel showing putative pAscAsc mini-prep DNAs cut with XmnI (lower right).

Figure 6:
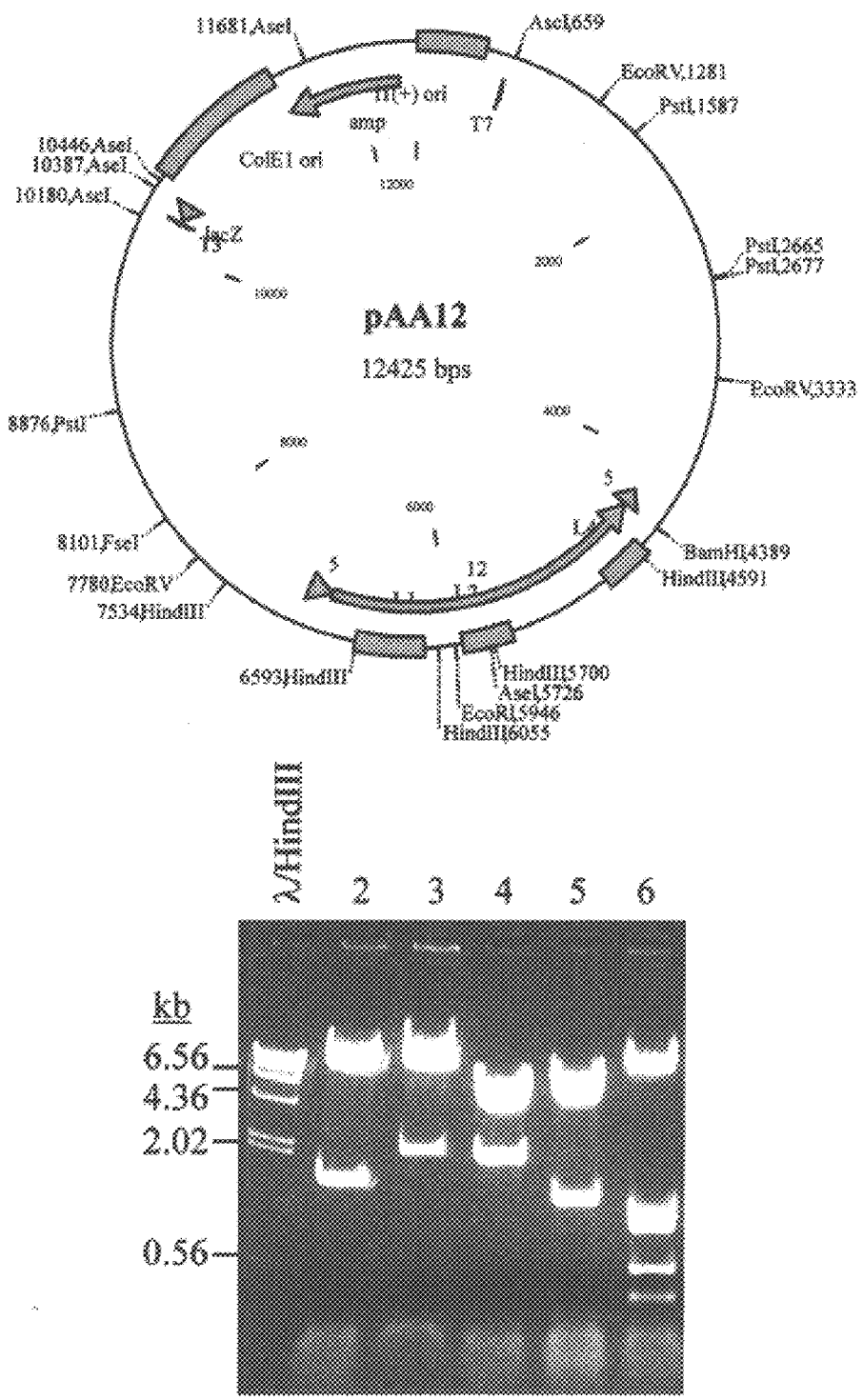

FIG. 6 shows a plasmid map of pAA12, and a gel showing a diagnostic digest of clone DNA of pAA12 digested with EcoRI and BamHI; EcoRI and FseI; EcoRV; AseI; and HindIII.

Figure 7:
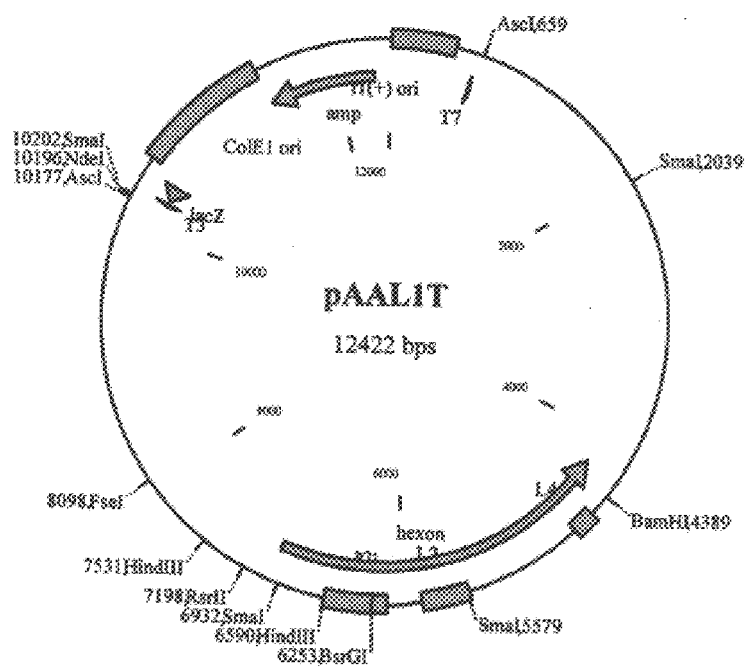
Figure 7:
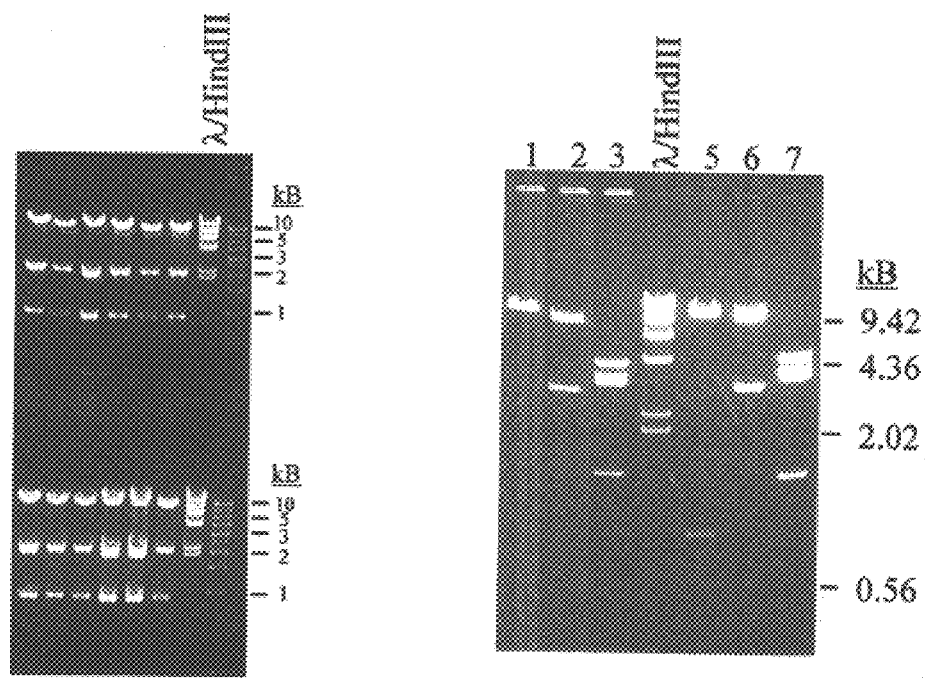

FIG. 7 shows a plasmid map of pAAL1T, a gel showing minipreps of two pABL1T clones which were double digested with HindIII and BamHI (lower left), and a gel showing a diagnostic digest of clone DNA of pAAL1T digested with HindIII, AscI, and SmaI (lower right).

Figure 8:
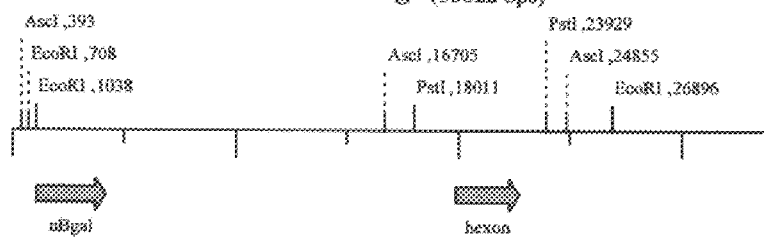
Figure 8:
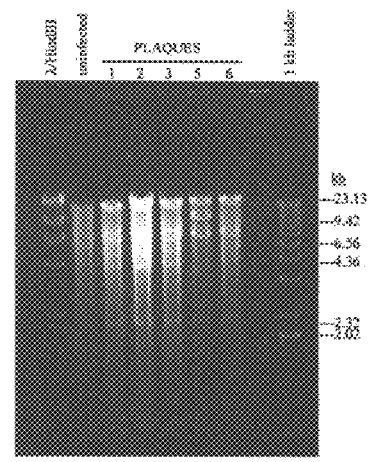
Figure 8:
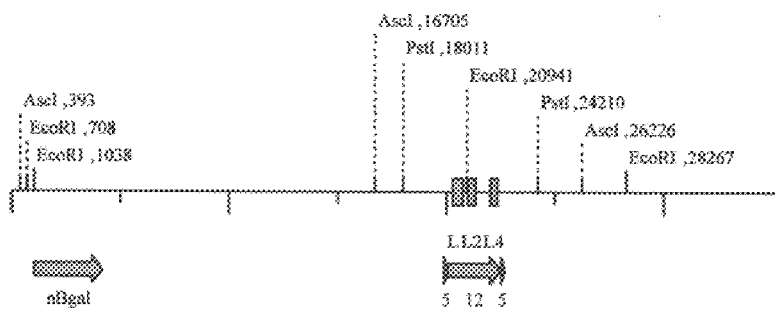
Figure 8:
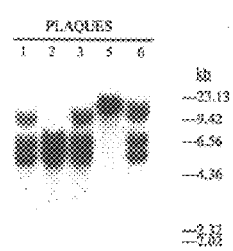

FIG. 8 shows maps of Av3nBg and Av12nBg, a gel showing DNA prepared from 293 cells infected with putative recombinant plaques digested with AscI and EcoRI and electrophoresed on a 0.7% agarose gel (upper right), and a Southern blot (lower right) of such gel probed with a radioactively labeled 6,199 base pair, DNA fragment derived from pAA12 extending from the PstI site at bp 2,677 to the PstI site at base pair 8,876.

Figure 9:
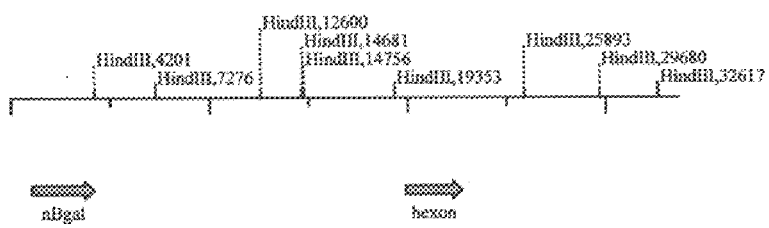
Figure 9:
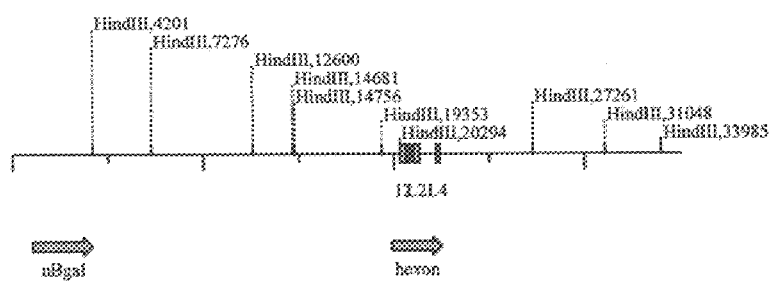
Figure 9:
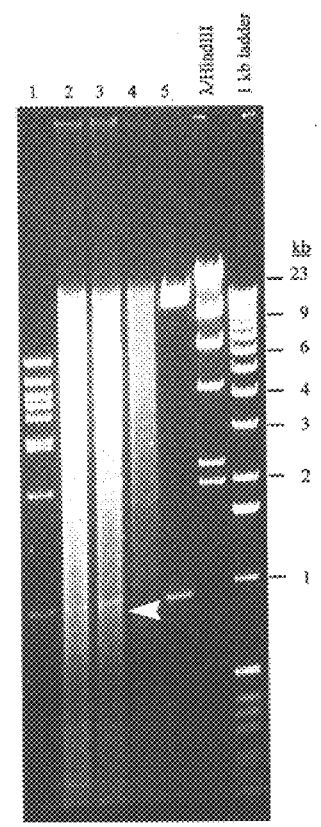
Figure 10:
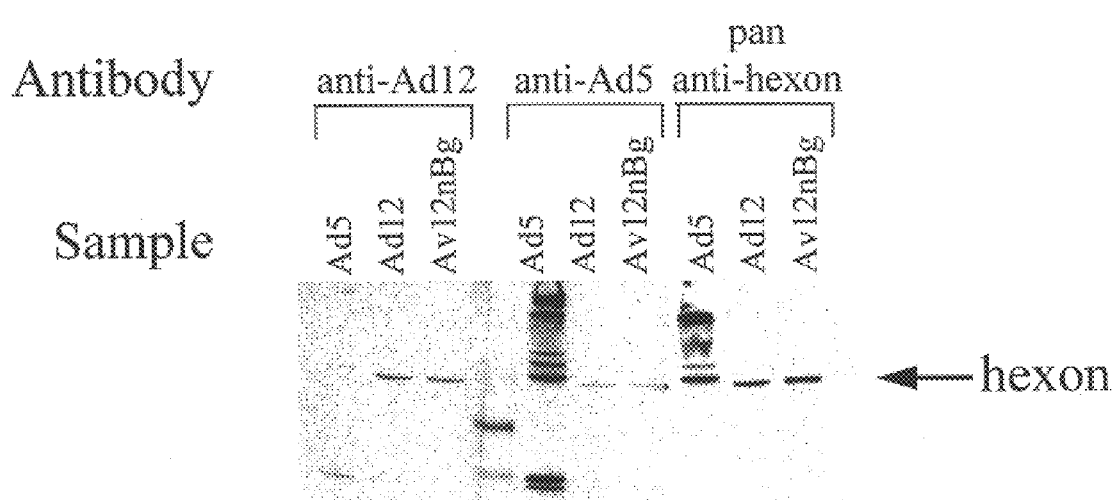

FIG. 9 shows maps of Av3nBg and Av13nBg, and a gel showing DNA prepared from 293 cells infected with putative recombinant plaques digested with HindIII and electrophoresed on a 0.7% agarose gel; and FIG. 10 is a Western Blot comparing anti-hexon reactivities of anti-Adenovirus 12, anti-Adenovirus 5, and monoclonal anti-hexon antibodies to proteins from pure virus preparations of Adenovirus 5, Adenovirus 12, and the chimeric virus Av12nBg.

DETAILED DESCRIPTION OF THE INVENTION

In accordance with an aspect of the present invention, there is provided an adenovirus wherein at least a portion of at least one loop region of the hexon is changed.

In one embodiment, the adenovirus, prior to modification, is of a first serotype, and at least a portion of at least one loop region of the hexon of the adenovirus is removed and replaced with at least a portion of at least one loop region of the hexon of an adenovirus of a second serotype. In another embodiment, all of at least one loop region of the hexon of the adenovirus of the first serotype is removed and replaced with at least one loop region of the hexon of an adenovirus of a second serotype.

In a preferred embodiment, the at least one portion of at least one loop region of the hexon of the adenovirus of the first serotype is (are) a portion(s) of a loop region(s) which includes an epitope(s) which is (are) recognized by a neutralizing antibody(ies) to the adenovirus of the first serotype. By removing such epitopes and replacing them with polypeptides which are not recognized by neutralizing antibodies to the adenovirus of the first serotype, one constructs an adenovirus which resists inactivation by the immune system of the host.

Although the scope of the present invention is not intended to be limited to any theoretical reasoning, Applicant has found that when one administers an adenovirus of a particular serotype to a host, such administration of the adenovirus elicits a neutralizing antibody(ies), which recognize an epitope(s) of the loop region(s) of the hexon. The neutralizing antibody(ies) is (are) serotype specific. By replacing the loop region(s) of the hexon with loop region(s) obtained from an adenovirus of a different serotype, the modified adenovirus, when administered to a host, will not be inactivated by the neutralizing antibody(ies) which specifically recognize the loop region(s) of the hexon of the adenovirus of the first serotype. Thus, the modified adenovirus, which preferably also includes at least one DNA sequence encoding a therapeutic agent, may be administered to the host without being inactivated by the immune system of the host. In accordance with the present invention, one may construct a series or battery of adenoviruses having a variety of altered or chimeric hexon proteins. The construction of such a series or battery of adenoviruses thus enables the repeated administration of recombinant adenoviruses to a host, while avoiding inactivation of the adenoviruses by the immune system of the host upon each administration of a recombinant adenovirus.

In yet another embodiment, at least a portion of at least one of the L1 and L2 loop regions of the hexon of the adenovirus of the first serotype is removed and replaced with at least a portion of at least one of the L1 and L2 loop regions of the hexon of the adenovirus of the second serotype. In another embodiment, all of at least one of the L1 and L2 loop regions of the hexon of the adenovirus of the first serotype is removed and replaced with all of at least one of the L1 and L2 loop regions of the hexon of the adenovirus of the second serotype. In a further embodiment, at least a portion of each of the L1, L2, and L4 loop regions of the hexon of the adenovirus of the first serotype is removed and replaced with at least a portion of each of the L1, L2, and L4 loop regions of the hexon of the adenovirus of the second serotype. In yet another embodiment, the L1, L2, and L4 loop regions of the hexon of the adenovirus of the first serotype are removed and replaced with the L1, L2, and L4 loop regions of the hexon of the adenovirus of the second serotype. In one embodiment, the first and second serotypes are from different adenovirus serotype subgenera.

In general, the human adenovirus serotypes are divided into Subgenera A through F. Such subgenera are described further in Bailey, et al., *Virology*, Vol. 205, pgs. 438–452 (1994), the contents of which are herein incorporated by reference. Subgenus A includes Adenovirus 12, Adenovirus 18, and Adenovirus 31. Subgenus B includes Adenovirus 3, Adenovirus 7, Adenovirus 34, and Adenovirus 35. Subgenus C includes Adenovirus 1, Adenovirus 2, Adenovirus 5, and Adenovirus 6. Subgenus D includes Adenovirus 9, Adenovirus 10, Adenovirus 15, and Adenovirus 19. Subgenus E includes Adenovirus 4. Subgenus F includes Adenovirus 40 and Adenovirus 41. In one embodiment, the adenovirus of the first serotype is an adenovirus of a serotype within Subgenus C, and the adenovirus of the second serotype is an adenovirus of a serotype within one of Subgenera A, B, D, E, or F, and preferably within one of Subgenera A or F. In another embodiment, the adenovirus of the first serotype is an adenovirus of a serotype selected from the group consisting of Adenovirus 2 and Adenovirus 5.

In general, it is preferred that the at least a portion of the loop region(s) of the hexon which is (are) removed from the adenovirus is (are) replaced with loop region(s) from an adenovirus of a serotype where there is minimal conservation of the loop region(s) of the hexons of the adenoviruses of the different serotypes. For example, at least a portion of at least one loop region of the hexon of Adenovirus 5 is removed and replaced with at least a portion of at least one loop region of the hexon of Adenovirus 12. Applicant has found unexpectedly, that although there is minimal conservation of the loop region(s) of the adenoviruses of the different serotypes, such as the pair(s) of adenovirus serotypes hereinabove described, one is able to construct and generate successfully adenoviruses wherein the adenovirus in general is from a first serotype, and the loop region(s) of the hexon is (are) removed and replaced with the loop region(s) of the hexon of an adenovirus of a second serotype wherein there is minimal conservation of the loop region(s) of the hexons of the adenoviruses of the different serotypes. It is to be understood, however, that the scope of the present invention is not to be limited to adenoviruses of any particular serotypes.

Such adenoviruses may be constructed from an adenoviral vector of a first serotype wherein DNA encoding at least a portion of at least one loop region of the hexon is removed and replaced with DNA encoding at least a portion of at least one loop region of the hexon of an adenovirus of a second serotype.

The adenovirus, in general, also includes at least one DNA sequence encoding a therapeutic agent. The term "therapeutic" is used in a generic sense and includes treating agents, prophylactic agents, and replacement agents.

DNA sequences encoding therapeutic agents include, but are not limited to, DNA sequences encoding tumor necrosis factor (TNF) genes, such as TNF-A; genes encoding interferons such as Interferon-α, Interferon-β, and Interferon-T; genes encoding interleukins such as IL-1, IL-1β, and Interleukins 2 through 14; genes encoding GM-CSF; genes encoding ornithine transcarbamylase, or OTC; genes encoding adenosine deaminase, or ADA; genes which encode cellular growth factors, such as lymphokines, which are growth factors for lymphocytes; genes encoding epidermal growth factor (EGF), and keratinocyte growth factor (KGF); genes encoding soluble CD4; Factor VIII; Factor IX; cytochrome b; glucocerebrosidase; T-cell receptors; the LDL receptor, ApoE, ApoC, ApoAI and other genes involved in cholesterol transport and metabolism; the alpha-1 antitrypsin (alAT) gene; the insulin gene; the hypoxanthine phosphoribosyl transferase gene; negative selective markers or "suicide" genes, such as viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, antisense sequences which inhibit viral replication, such as antisense sequences which inhibit replication of hepatitis B or hepatitis non-A non-B virus; antisense c-myb oligonucleotides; and antioxidants such as, but not limited to, manganese superoxide dismutase (Mn-SOD), catalase, copper-zinc-superoxide dismutase (CuZn-SOD), extracellular superoxide dismutase (EC-SOD), and glutathione reductase; tissue plasminogen activator (tPA); urinary plasminogen activator (urokinase); hirudin; the phenylalanine hydroxylase gene; nitric oxide synthetase; vasoactive peptides; angiogenic peptides; the dopamine gene; the dystrophin gene; the α-globin gene; the α-globin gene; the HbA gene; protooncogenes such as the ras, src, and bcl genes; tumor-suppressor genes such as p53 and Rb; the heregulin-α protein gene, for treating breast, ovarian, gastric and endometrial cancers; monoclonal antibodies specific to epitopes contained within the β-chain of a T-cell antigen receptor; the multidrug resistance (MDR) gene; DNA sequences encoding ribozymes; antisense polynucleotides; genes encoding secretory peptides which act as competitive inhibitors of angiotensin converting enzyme, of vascular smooth muscle calcium channels, or of adrenergic receptors, and DNA sequences encoding enzymes which break down amyloid plaques within the central nervous system. It is to be understood, however, that the scope of the present invention is not to be limited to any particular therapeutic agent.

The DNA sequence which encodes the therapeutic agent may be genomic DNA or may be a cDNA sequence. The DNA sequence also may be the native DNA sequence or an allelic variant thereof. The term "allelic variant" as used herein means that the allelic variant is an alternative form of the native DNA sequence which may have a substitution, deletion, or addition of one or more nucleotides, which does not alter substantially the function of the encoded protein or polypeptide or fragment or derivative thereof. In one embodiment, the DNA sequence may further include a leader sequence or portion thereof, a secretory signal or portion thereof and/or may further include a trailer sequence or portion thereof.

The DNA sequence encoding at least one therapeutic agent is under the control of a suitable promoter. Suitable promoters which may be employed include, but are not limited to, adenoviral promoters, such as the adenoviral major late promoter; or heterologous promoters, such as the cytomegalovirus (CMV) promoter; the Rous Sarcoma Virus (RSV) promoter; inducible promoters, such as the MMT promoter, the metallothionein promoter; heat shock promoters; the albumin promoter; and the ApoAI promoter. It is to be understood, however, that the scope of the present invention is not to be limited to specific foreign genes or promoters.

The adenoviral vector which is employed may, in one embodiment, be an adenoviral vector which includes essentially the complete adenoviral genome (Shenk et al., Curr. Top. Microbiol. Immunol., 111(3): 1–39 (1984). Alternatively, the adenoviral vector may be a modified adenoviral vector in which at least a portion of the adenoviral genome has been deleted.

In a preferred embodiment, the adenoviral vector comprises an adenoviral 5' ITR; an adenoviral 3' ITR; an adenoviral encapsidation signal; a DNA sequence encoding a therapeutic agent; and a promoter controlling the DNA sequence encoding a therapeutic agent. The vector is free of at least the majority of adenoviral E1 and E3 DNA sequences, but is not free of all of the E2 and E4 DNA sequences, and DNA sequences encoding adenoviral proteins promoted by the adenoviral major late promoter.

In one embodiment, the vector also is free of at least a portion of at least one DNA sequence selected from the group consisting of the E2 and E4 DNA sequences.

In another embodiment, the vector is free of at least the majority of the adenoviral E1 and E3 DNA sequences, and is free of a portion of the other of the E2 and E4 DNA sequences.

In still another embodiment, the gene in the E2a region that encodes the 72 kilodalton binding protein is mutated to produce a temperature sensitive protein that is active at 32° C., the temperature at which the viral particles are produced. This temperature sensitive mutant is described in Ensinger et al., J. Virology, 10:328–339 (1972), Van der Vliet et al., J. Virology, 15:348–354 (1975), and Friefeld et al., Virology, 124:380–389 (1983).

Such a vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a multiple cloning site (which may be as herein described); a poly A signal; and a DNA segment which corresponds to a segment of the adenoviral genome. The vector also may contain a tripartite leader sequence. The DNA segment corresponding to the adenoviral genome serves as a substrate for homologous recombination with a modified or mutated adenovirus, and such sequence may encompass, for example, a segment of the adenovirus 5 genome no longer than from base 3329 to base 6246 of the genome. The plasmid may also include a selectable marker and an origin of replication. The origin of replication may be a bacterial origin of replication. Representative examples of such shuttle plasmids include pAvS6, which is described in published PCT Application Nos. WO94/23582, published Oct. 27, 1994, and WO95/09654, published Apr. 13, 1995 and in U.S. Pat. No. 5,543,328, issued Aug. 6, 1996. The DNA sequence encoding a therapeutic agent then may be inserted into the multiple cloning site to produce a plasmid vector.

This construct is then used to produce an adenoviral vector. Homologous recombination is effected with a modified or mutated adenovirus in which at least the majority of the E1 and E3 adenoviral DNA sequences have been deleted. Such homologous recombination may be effected through cotransfection of the plasmid vector and the modified adenovirus into a helper cell line, such as 293 cells, by $CaPO_4$ precipitation. Upon such homologous recombination, a recombinant adenoviral vector is formed that includes DNA sequences derived from the shuttle plasmid between the Not I site and the homologous recombination fragment, and DNA derived from the E1 and E3 deleted adenovirus between the homologous recombination fragment and the 3' ITR.

In one embodiment, the homologous recombination fragment overlaps with nucleotides 3329 to 6246 of the adenovirus 5 (ATCC VR-5) genome.

Through such homologous recombination, a vector is formed which includes an adenoviral 5' ITR, an adenoviral encapsidation signal; an E1a enhancer sequence; a promoter; a DNA sequence encoding a therapeutic agent; a poly A signal; adenoviral DNA free of at least the majority of the E1 and E3 adenoviral DNA sequences; and an adenoviral 3' ITR. The vector also may include a tripartite leader sequence. The vector may then be transfected into a helper cell line, such as the 293 helper cell line (ATCC No. CRL1573), which will include the E1a and E1b DNA sequences, which are necessary for viral replication, and to generate adenoviral particles. Transfection may take place by electroporation, calcium phosphate precipitation, microinjection, or through proteoliposomes.

In another embodiment, the adenoviral vector is free of all or a portion of each of the adenoviral E1 and E4 DNA sequences, or is free of all or a portion of each of the adenoviral E1 and E2 DNA sequences, or is free of all or a portion of each of the E1, E2, and E4 DNA sequences.

Such vectors may be assembled by direct in vitro ligation from combinations of plasmids containing portions of modified or unmodified virus genome or plasmids and fragments derived directly from a linear adenoviral genome, such as the Adenovirus 5 genome (ATCC No. VR-5) or Adenovirus 5 derived viruses containing mutations or deletions.

In another alternative, the vectors can be assembled by homologous recombination, within a eukaryotic cell, between a plasmid clone containing a portion of the adenoviral genome (such as the Adenovirus 5 genome or the adenovirus 5 E3-mutant Ad dl327 (Thimmapaya, et al., *Cell*, Vol. 31, pg. 543 (1983)) with the desired modifications, and a second plasmid (such as, for example pAvS6), containing the left adenoviral ITR, an E1 region deletion, and the desired trans gene. Alternatively, homologous recombination may be carried out between a plasmid clone and a fragment derived directly from a linear adenovirus (such as Adenovirus 5, or Ad dl327 or an Adenovirus 5 derived virus containing mutations or deletions) genome.

The vector then is transfected into a cell line capable of complementing the function of any essential genes deleted from the viral vector, in order to generate infectious viral particles. The cell line in general is a cell line which is infectable and able to support adenovirus or adenoviral vector growth, provide for continued virus production in the presence of glucocorticoid hormones, and is responsive to glucocorticoid hormones (i.e., the cell line is capable of expressing a glucocorticoid hormone receptor). Cell lines which may be transfected with the essential adenoviral genes, and thus may be employed for generating the infectious adenoviral particles include, but are not limited to, the A549, KB, and Hep-2 cell lines.

Because the expression of some viral genes may be toxic to cells, the E1 region, as well as the E2a, E2b, and/or E4 regions, may be under the control of an inducible promoter. Such inducible promoters may include, but are not limited to, the mouse mammary tumor virus (MMTV) promoter (Archer, et al., *Science*, Vol. 255, pgs. 1573–1576 (Mar. 20, 1992)); the synthetic minimal glucocorticoid response element promoter GRE5 (Mader, et al., *Proc. Nat. Acad. Sci.*, Vol. 90, pgs. 5603–5607 (June 1993)); or the tetracycline-responsive promoters (Gossen, et al., *Proc. Nat. Acad. Sci.*, Vol. 89, pgs. 5547–5551 (June 1992)). In another alternative, the E1 region is under the control of an inducible promoter, and the E1 E2a, E2b and/or E4 regions are under the control of their native promoters. In such alternative, the native promoters are transactivated by expression of the E1 region.

In one embodiment, the cell line includes the entire adenoviral E4 region with its native promoter region, and the E1a region or the entire E1 region (including the E1a and E1b regions) under the control of a regulatable or inducible promoter, such as, for example, the mouse mammary tumor virus (or MMTV) promoter, which is a hormone inducible promoter, or other such promoters containing glucocorticoid responsive elements (GRE's) for transcriptional control. In another embodiment, the E4 DNA sequence also is expressed from a regulatable promoter, such as the MMTV promoter. The E1 and E4 DNA sequences may be included in one expression vehicle, or may be included in separate expression vehicles. Preferably, the expression vehicles are plasmid vectors which integrate with the genome of the cell line.

Such vectors, wherein the vector is free of all or a portion of each of the adenoviral E1 and E4 DNA sequences, or is free of all or a portion of each of the adenoviral E1 and E2 DNA sequences, or is free of all or a portion of the E1, E2, and E4 DNA sequences, and the complementing cell lines, also are described in PCT Application No. WO96/18418, published Jun. 20, 1996, the contents of which are incorporated herein by reference.

Upon formation of the adenoviral vectors hereinabove described, the genome of such a vector is modified such that DNA encoding at least a portion of at least one loop region os the hexon is removed and replaced with DNA encoding at least a portion of at least one loop region of the hexon of an adenovirus having a serotype different from that of the adenovirus being modified. Such modification may be accomplished through genetic engineering techniques known to those skilled in the art.

Upon modification of the genome of the adenoviral vector, the vector is transfected into an appropriate cell line for the generation of infectious adenoviral particles wherein at least a portion of at least one loop region of the hexon has been changed.

Alternatively, the DNA sequence encoding the modified hexon may be placed into an adenoviral shuttle plasmid such as those hereinabove described. The shuttle plasmid also may include a DNA sequence encoding a therapeutic agent. The shuttle plasmid is transfected into an appropriate cell line for the generation of infectious viral particles, with an adenoviral genome wherein the DNA encoding the hexon is deleted.

In another alternative, a first shuttle plasmid includes the DNA sequence encoding the modified hexon, and a second shuttle plasmid includes a DNA sequence encoding a therapeutic agent. The shuttle plasmids are cotransfected into an appropriate cell line for the generation of infectious viral particles, with an adenoviral genome wherein the DNA encoding the hexon is deleted. Homologous recombination produces an adenoviral vector including a modified hexon protein.

The adenoviruses of the present invention may be administered to a host in vivo in an amount effective to provide a therapeutic effect in a host.

In one embodiment, the adenoviral vector may be administered in an amount of from 1 plaque forming unit to about $10^{14}$ plaque forming units, preferably from about $10^6$ plaque forming units to about $10^{13}$ plaque forming units. The host may be a mammalian host, including human or non-human primate hosts.

The infectious adenoviral vectors are administered to the lung when a disease or disorder of the lung (such as, for example, cystic fibrosis) is to be treated. Such administration may be, for example, by aerosolized inhalation or brochoscopic instillation, or via intranasal or intratracheal instillation.

In another embodiment, the infectious adenoviral vectors are administered systemically, such as, for example, by intravenous administration (such as, for example, portal vein injection or peripheral vein injection), intraarterial administration, intramuscular administration, intraperitoneal administration, intratracheal administration, or intranasal administration.

The adenoviral vectors may be administered in combination with a pharmaceutically acceptable carrier suitable for administration to a patient. The carrier may be a liquid carrier (for example, a saline solution), or a solid carrier, such as, for example, microcarrier beads.

Cells which may be infected by the infectious adenoviral vectors include, but are not limited to, primary cells, such as primary nucleated blood cells, such as leukocytes, granulocytes, monocytes, macrophages, lymphocytes (including T-lymphocytes and B-lymphocytes), totipotent stem cells, and tumor infiltrating lymphocytes (TIL cells); bone marrow cells; endothelial cells; activated endothelial cells; epithelial cells; lung cells; keratinocytes; stem cells; hepatocytes, including hepatocyte precursor cells; fibroblasts; mesenchymal cells; mesothelial cells; parenchymal cells; vascular smooth muscle cells; brain cells and other neural cells; gut enterocytes; gut stem cells; and myoblasts.

The infected cells are useful in the treatment of a variety of diseases including but not limited to adenosine deaminase deficiency, sickle cell anemia, thalassemia, hemophilia A, hemophilia B, diabetes, a-antitrypsin deficiency, brain disorders such as Alzheimer's disease, phenylketonuria and other illnesses such as growth disorders and heart diseases, for example, those caused by alterations in the way cholesterol is metabolized and defects of the immune system.

In one embodiment, the adenoviral vectors may be used to infect lung cells, and such adenoviral vectors may include the CFTR gene, which is useful in the treatment of cystic fibrosis. In another embodiment, the adenoviral vector may include a gene(s) encoding a lung surfactant protein, such as SP-A, SP-B, or SP-C, whereby the adenoviral vector is employed to treat lung surfactant protein deficiency states.

In another embodiment, the adenoviral vectors may be used to infect liver cells, and such adenoviral vectors may include gene(s) encoding clotting factor(s), such as Factor VIII and Factor IX, which are useful in the treatment of hemophilia A and hemophilia B, respectively.

In another embodiment, the adenoviral vectors may be used to infect liver cells, and such adenoviral vectors may include gene(s) encoding polypeptides or proteins which are useful in prevention and therapy of an acquired or an inherited defect in hepatocyte (liver) function. For example, they can be used to correct an inherited deficiency of the low density lipoprotein (LDL) receptor, or a deficiency of ornithine transcarbamylase.

In another embodiment, the adenoviral vectors may be used to infect liver cells, whereby the adenoviral vectors include a gene encoding a therapeutic agent employed to treat acquired infectious diseases, such as diseases resulting from viral infection. For example, the infectious adenoviral vectors may be employed to treat viral hepatitis, particularly hepatitis B or non-A non-B hepatitis. For example, an infectious adenoviral vector containing a gene encoding an anti-sense gene could be employed to infect liver cells to inhibit viral replication. In this case, the infectious adenoviral vector, which includes a structural hepatitis gene in the reverse or opposite orientation, would be introduced into liver cells, resulting in production in the infected liver cells of an anti-sense gene capable of inactivating the hepatitis virus or its RNA transcripts. Alternatively, the liver cells may be infected with an infectious adenoviral vector which includes a gene which encodes a protein, such as, for example, α-interferon, which may confer resistance to the hepatitis virus.

In yet another embodiment, an adenoviral vector in accordance with the present invention may include a negative selective marker, or "suicide" gene, such as the Herpes Simplex Virus thymidine kinase (TK) gene. Such a vector may be employed in the treatment of tumors, including cancerous and non-malignant tumors, by administering the adenoviral vector to a patient, such as, for example, by direct injection of the adenoviral vector into the tumor, whereby the adenoviral vector transduces the tumor cells. After the cells are transduced with the adenoviral vector, an interaction agent or prodrug, such as, for example, ganciclovir, is administered to the patient, whereby the transduced tumor cells are killed.

In another embodiment, the adenoviral vectors, which include at least one DNA sequence encoding a therapeutic agent, may be administered to an animal in order to use such animal as a model for studying a disease or disorder and the treatment thereof. For example, an adenoviral vector containing a DNA sequence encoding a therapeutic agent may be given to an animal which is deficient in such therapeutic agent. Subsequent to the administration of such vector containing the DNA sequence encoding the therapeutic agent, the animal is evaluated for expression of such therapeutic agent. From the results of such a study, one then may determine how such adenoviral vectors may be administered to human patients for the treatment of the disease or disorder associated with the deficiency of the therapeutic agent.

EXAMPLES

The invention now will be described with respect to the examples; however, the scope of the present invention is not intended to be limited thereby.

Example 1

Construction of chimeric viruses based on Adenovirus 5 with hexons derived from Adenovirus 12

A. Cloning of Ad dl327 fragment into pNEB193

Figure 2:
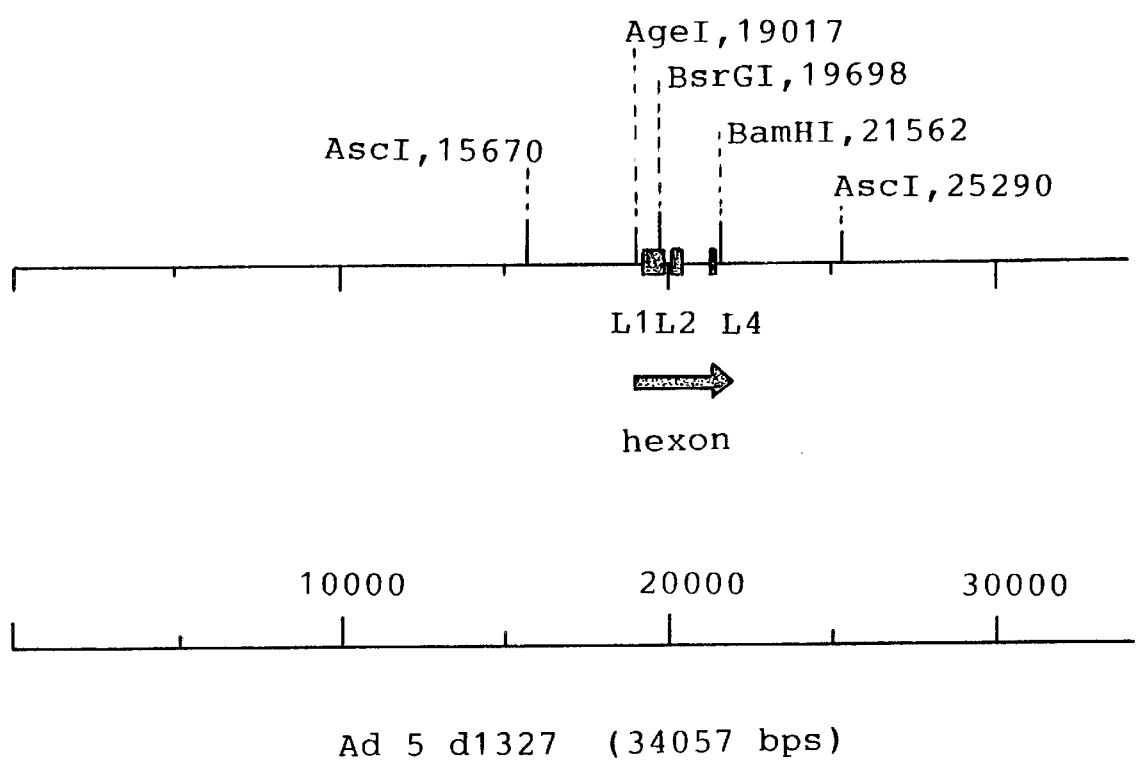
Figure 3:
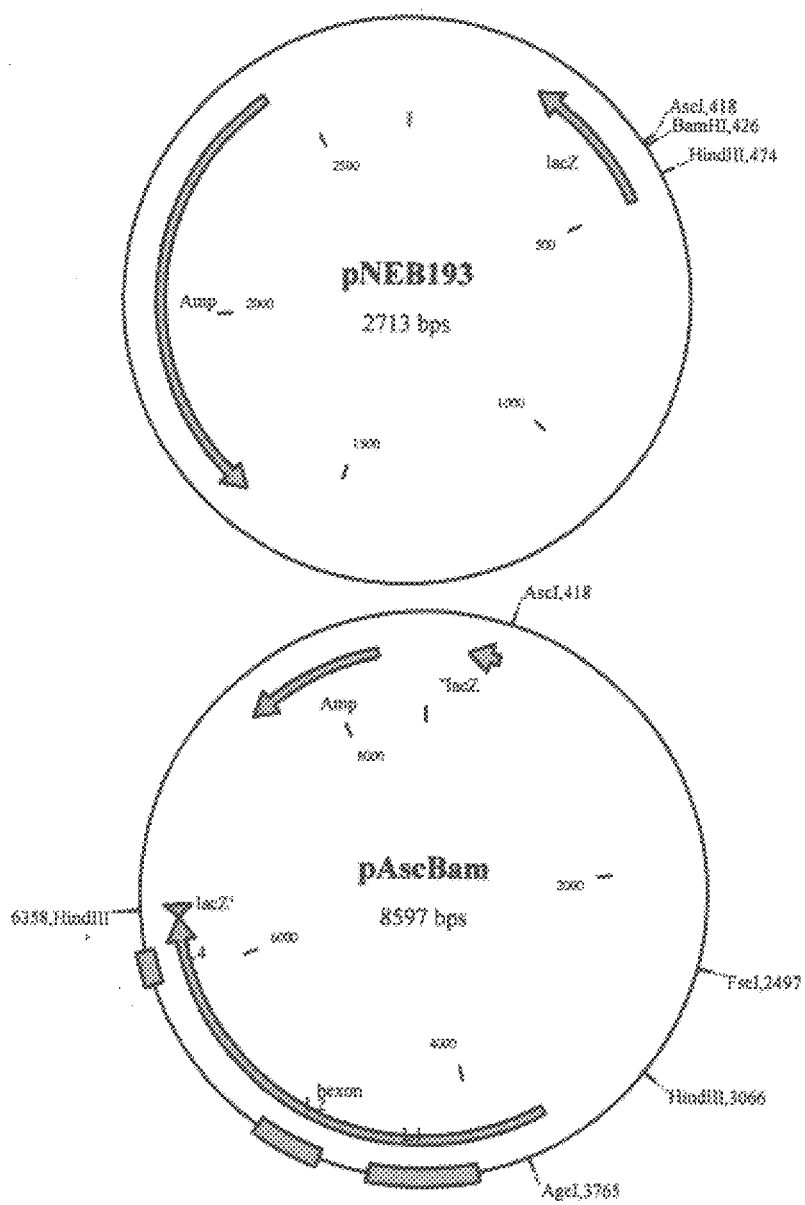
FIG. 3 shows the maps of plasmids pNEB193 and pAscBam, and a gel showing miniprep DNAs cut with HindIII.
Figure 3:
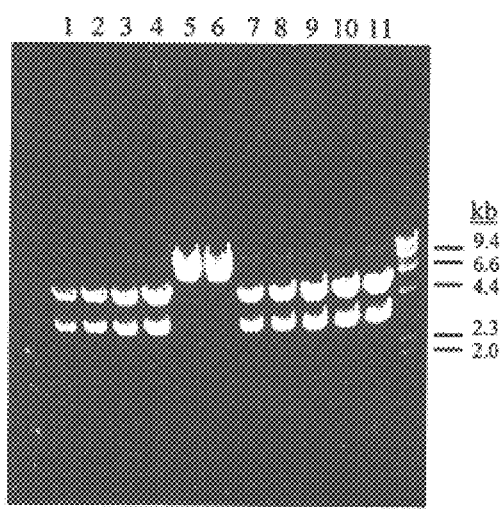

Ad dl327 (Thimmappaya, Cell, Vol. 31, pg. 543 (1983), incorporated herein by reference) is identical to Adenovirus 5 (Genbank Accession #M73260), except that an XbaI fragment including bases 28591 to 30474 (or map units 78.5 to 84.7) of the Adenovirus 5 genome, and which is located in the E3 region, has been deleted. A schematic of Ad dl327 is shown in FIG. 2. Ad dl327 was cut with AscI and BamHI, and a fragment from base 15670 to base 21562, which includes the hexon of Adenovirus 5 was isolated. This fragment was cloned into pNEB193 (New England Biolabs) (FIG. 3), which was cut with AscI and BamHI. Twelve miniprep DNA's of the resulting construct, cut with HindIII, were prepared. The minipreps were made using the boiling lysis method as described by Sambrook, et al., *Molecular Cloning, A Laboratory Manual*, Vol. 1, pgs. 29–30, Cold Spring Harbor Laboratory Press (1989). About 500 ng of each DNA miniprep was digested with restriction enzymes and electrophoresed on agarose gels using standard procedures. One clone, clone number 11, pAscBam (FIG. 3), was chosen for further experimentation.

B. PCR of Adenovirus 12 sequences and cloning of the amplified products

FIG. 1A shows the alignment of the predicted hexon amino acid sequences (based on published nucleotide sequences) of human Adenovirus 12 (SEQ ID NO:4) and human Adenovirus 5. (SEQ ID NO:5) The alignment of Adenovirus 5 (SEQ ID NO:7)and Adenovirus 12 (SEQ ID NO:6)hexon (and flanking) nucleotide sequences are shown in FIG. 1B. Because the AgeI recognition sequence (ACCGGT) is not preserved in Adenovirus 12, this sequence was synthesized as a leader into one of the PCR primers used for this amplification (SZR46—GCG ACC GGT CGC AGC GTC TGA CGC TGC GT) (SEQ ID NO:1). The BamHI site, however, is present in the Adenovirus 12 sequence. The downstream primer (SZR45—GTG AAT GCG TAC CAC GTC G) (SEQ ID NO:2)that was synthesized was positioned downstream of the BamHI site (FIG. 1B).

The PCR was carried out with the Elongase PCR Kit (Life Technologies, Inc., Gaithersburg, MD) exactly according to the manufacturer's instructions. The PCR mixture contained 50 ng of purified Adenovirus 12 DNA template, 200 µM of each deoxynucleoside triphosphate, 0.2 µM of each primer, Elongase buffer containing 1.6 mM $Mg^{2+}$ and Elongase enzyme mixture in a 50 µl total volume. The samples were placed in a Perkin-Elmer thermocycler and subjected to PCR amplification as follows:

1. Pre-amplification denaturation: 94° C. for 30 seconds;
2. Thermal cycling for 30 cycles: denaturation—94° C. for 30 seconds annealing—55° C. for 30 seconds; extension—68° C. for 7.5 minutes.
3. Hold at 4° C.

The 2,507 bp PCR product was double digested with AgeI and BamHI, and cloned in between the AgeI and BamHI sites of pAscBam to generate pAB12 (FIG. 4A) DNA minipreps (numbered 8 through 18 from lane 3 as shown in FIG. 4A, left to right) were digested with HindIII. All except clone number 14 showed the expected restriction pattern. Clones 12, 13, 15, and 16 were sequenced for about 300 bases from and including the upstream primer SZR46 hereinabove described. All four sequences were correct in and around the upstream primer. Clone 12 was used for further manipulations.

C. PCR of Adenovirus 12 sequence corresponding to most of the L1 loop (574 bp) and cloning of the amplified product The primer SZR46 was synthesized as hereinabove described. The BsrGI site is located 5' to the end of the L1 region but is 3' to the most variable part of L1. The downstream primer (SZR57—CGG TGT ACA ACA CAA CTT GAG CAG TGT TTG C) (SEQ ID NO:3)was synthesized to incorporate and overlap the BsrGI site. (FIG. 1B) This PCR was accomplished using Taq polymerase. The PCR mixture contained 50 ng of purified Adenovirus 12 DNA template, 200 µM of each deoxynucleoside triphosphate, 0.2 µM of each primer, Taq polymerase buffer (Boehringer Mannheim), and Taq polymerase enzyme in a 50 µl total volume. The samples were placed in a Perkin-Elmer thermocycler and subjected to PCR amplification as follows:

1. Pre-amplification denaturation: 95° C. for 3 minutes.
2. Thermal cycling for 30 cycles: denaturation—94° C. for 30 seconds; annealing—50° C. for 30 seconds; extension—72° C. for 1 minute.
3. Hold at 4° C.

The PCR fragment was digested with AgeI and BsrGI and cloned in between these sites in pAscBam to generate PABL1T (FIG. 4B). The gel shown in FIG. 4B shows a digestion of six DNA minipreps with HindIII. All were correct. Clones 1 and 2 were chosen for further subcloning.

D. Cloning Ad dl327 DNA fragment into pCRScript Direct

Ad dl327 was cut with AscI, and the resulting DNA fragment from base 15670 to base 25290 was cloned into pCRScript Direct (Stratagene, La Jolla, Calif.) that was linearized with AscI. Twelve DNA minipreps were checked by digestion with XmnI. Clone number 2 was determined to have a forward orientation, pAscAscf (FIG. 5), and clone number 6 was determined to have a reverse orientation, pAscAscr (FIG. 5).

E. Replacement of the Adenovirus S hexon sequences pAscAscr was cut with FseI and BamHI and the 3,811 bp FseI-BamHI fragment of pAscAscr was replaced with the 3,714 bp FseI-BamHI fragment from pAB12 to generate pAA12 (FIG. 6). The gel shown in FIG. 6 shows a diagnostic digest of clone DNA with EcoRI and BamHI (lane 2—fragments of 10,868 and 1,557 base pairs), EcoRI and FseI (lane 3—fragments of 5,946 and 2,155 base pairs), EcoRV (lane 4—fragments of 5,926, and 4,447, and 2,052 base pairs), AseI (lane 5—fragments of 6,470, and 4,661, and 1,235, and 59 base pairs), and HindIII (lane 6—fragments of 9,482, and 1,109, and 941, and 538, and 355 base pairs).

In another construction, the 3,811 bp FseI-BamHI fragment of pAscAscr was replaced with the 3,711 bp FseI-BamHI fragment from PABL1T to generate pAAL1T (FIG. 7). Two clones (numbers 1 and 2 of PABL1T) were used as donors for the cloning. Six DNA minipreps were made from each cloning/transformation. The gel shown in FIG. 7 (lower left) shows diagnostic digests of the minipreps. (Top row—6 minipreps derived from PABL1T clone 1; bottom row—6 minipreps derived from PABL1T clone 2). The DNAs were double digested with HindIII and BamHI (expected fragment sizes of 9,280, and 2,201, and 941 bp). The gel shown in FIG. 7 (lower right) shows a diagnostic digest of the chosen clone DNA of pAAL1T digested with HindIII (lane 5, expected fragment sizes of 11,481 and 941 bp), AscI (lane 6, expected fragment sizes of 9,518 and 2,904 bp), and SmaI (lane 7, expected fragment sizes of 4,259, and 3,540, and 3,270, and 1,353 bp). Digests of pAscAscr with the same enzymes were run in lanes 1, 2, and 3 for comparison.

F. Replacement of the natural (wild type) Adenovirus 5 hexon in the adenovirus vector Av3nBg with the chimeric hexon constructs The adenoviral vector Av3nBg is identical to the adenoviral vector Av3nLacZ, described in PCT Application No. WO096/18418, published June 20, 1996. Such vector has the genotype E1⁻ E2⁻ E3⁻ E4⁺; i.e., such vector has deletions of the E1, E2a, and E3 DNA sequences.

Av3nBg DNA was digested with AscI, followed by destruction of AscI enzyme activity by digestion with Proteinase K.

pAA12 was digested with AscI, and a 9,521 bp fragment was gel purified. This fragment contains a chimeric hexon construct where the loop regions L1, L2, and L4 of Adenovirus 5 have been replaced with the L1, L2, and L4 loop regions of Adenovirus 12.

pAAL1T was digested with AscI, and a 9,518 bp fragment was gel purified. This fragment contains a chimeric hexon construct where most of the L1 loop region of Adenovirus 5 hexon has been replaced with the L1 loop region from Adenovirus 12.

Each of the gel purified AscI fragments from pAA12 and from pAAL1T were ligated into the AscI digested Av3nBg DNA.

Each of the ligation products was transfected into 293 cells. Because Av3nBg DNA has a deletion of the E2a region which cannot be complemented in 293 cells, this transfection should select for recombinant adenovirus where the E2a function is present. Because the AscI fragments containing the chimeric hexon constructs contain an intact E2a region, this procedure exerts a biological selection for adenovirus recombinants containing the chimeric hexon.

G. Analysis of plaques (i) Replacement of L1, L2, and L4 loop regions of Adenovirus 5 with homologous regions from Adenovirus 12

Five plaques were picked and amplified on 293 cells. DNA was isolated from the infected cells and digested with a combination of AscI and EcoRI, electrophoresed on a 0.7% agarose gel (FIG. 8, upper right), and subjected to Southern blotting. The Southern blot was probed with a radioactively labeled probe made from a purified 6,199 bp fragment derived from pAA12, extending from the PstI site at base pair 2,677 to the PstI site at base pair 8,876. A map of Av3nBg showing the restriction sites for AscI and EcoRI, and a map of the desired recombinant virus (Av12nBg) are shown in FIG. 8. The autoradiograph showing the result of the hybridization is shown in FIG. 8 (lower right). The parent vector Av3nBg is expected to produce a hybridizing fragment having a size of 8,150 bp. The desired recombinant adenovirus, Av12nBg, with the chimeric hexon is expected to contain an EcoRI site within the hexon gene not present on the parent Adenovirus 5 hexon which would result in two hybridizing fragments of 5,285 and 4,236 base pairs, respectively. As seen in FIG. 8, DNA from the expanded plaques 1, 2, 3, and 6 display the predicted hybridization pattern. DNA from plaque number 2 also appears to be free largely of contaminating DNA. Therefore, plaque number 2 appears to be the desired recombinant adenovirus Av12nBg as shown in FIG. 8. (The last lane on the right contains plasmid pAscAscr digested with AscI and EcoRI. The top band probably corresponds to incompletely digested plasmid DNA.) This recombinant virus was plaque purified, and a pure preparation of virus was made by employing a standard adenovirus purification protocol. The preparation was plaque titered. This preparation was used for antibody reactivity experiments.

(ii) Replacement of most of the L1 loop region with the homologous region from Adenovirus 12

Seven plaques (numbers 3, 4, 5, 6, 7, 8, and 9) were picked and amplified on 293 cells. DNA was isolated from the infected cells and digested with HindIII and electrophoresed on a 0.7% agarose gel along with Av3nBg DNA/ HindIII and pAAL1T/HindIII (FIG. 9). Plaque number 9 shows the presence of the 941 bp band expected from the desired adenovirus recombinant (Av13nBg).

Example 2

Testing chimeric viruses for reduced reactivity to antibodies to Adenovirus 5

A. Western blotting

About $2\times10^9$ pfu of the virus Av12nBg was electrophoresed (in triplicate) alongside an equal amount of an Ad dl327 preparation and an Adenovirus 12 (ATCC No. VR-863) preparation. The sample buffer used for the electrophoresis contained 62.5mM Tris HCl, pH 6.8, 2% SDS, 1% glycerol, and 0.00125% bromophenol blue. The samples were not heated prior to electrophoresis. Under these conditions the hexon trimers do not separate into monomers. Following electrophoresis on a 4–15% polyacrylamide gradient gel, the separated proteins were electroblotted onto a PVDF membrane. The blot was cut into three identical strips, with each strip containing the three viruses being compared. The strips then were subjected to immunodetection using standard protocols. One strip was probed with a mouse monoclonal antibody (H467) with reactivity to all hexon serotypes. The probe was used at a concentration of 0.2 µg/ml. The two other strips were probed with serotype specific rabbit polyclonal antibodies to Adenovirus 5 (ATCC No. VR-1082 AS/Rab) and Adenovirus 12 (ATCC No. VR-1089 AS/Rab), respectively, at a 1:3,000 dilution. The Western Blot (FIG. 10) shows that, as expected, the monoclonal antibody recognized the hexon trimer complex from all three virus preparations, and the anti-Adenovirus 5 and anti-Adenovirus 12 antibodies have preferential reactivities to their cognate hexons. The chimeric hexon was detected more readily by the anti-Adenovirus 12 antibody than the anti-Adenovirus 5 antibody.

B. Neutralization assays

The neutralization assays were conducted as described by Smith, et al., Nature Genetics, Vol. 5, pgs. 397–402 (1993) using Av1LacZ4 and Av12nBg as input indicator viruses. An equal amount ($10^4$ pfu) of each virus was incubated with serial dilutions of plasma from individual C57/B16 mice which had been injected previously with an Adenovirus 5 based adenovirus vector. Following the incubation, the virus was used to infect 293 cells in 96 well plates. The next day, the cells ere stained for β-galactosidase expression by the indicator X-gal. In the absence of antibody, all the cells in the well showed β-galactosidase expression. The presence of neutralizing antibody in plasma is revealed by a reduction in the number of cells transduced by the indicator virus. The neutralization titer of each plasma was scored as the reciprocal of the dilution at which only about 25% of the cells in a well showed β-galactosidase expression. The results of three separate experiments are given in Tables I, II and III below.

TABLE I

| | Neutralization titer (about 25% blue cells) | |
|---|---|---|
| Mouse | Av1LacZ4 | Av12nBg |
| 1 | >1024 | <8 |
| 2 | >1024 | <8 |
| 3 | >1024 | <8 |
| 4 | >1024 | <8 |
| 5 | 256 | <8 |

TABLE II

| | Neutralization titer (about 25% blue cells) | |
|---|---|---|
| Mouse | Av1LacZ4 | Av12nBg |
| 1 | 256 | <2 |
| 2 | 8 | <2 |
| 3 | 64 | <2 |
| 4 | 256 | <2 |
| 5 | 256 | <2 |
| 6 | 1,024 | <2 |

TABLE III

| | Neutralization titer (about 25% blue cells) | |
|---|---|---|
| Mouse | Av1LacZ4 | Av12nBg |
| 1 | >512 | 16 |
| 2 | >512 | <4 |
| 3 | >512 | <4 |
| 4 | >512 | <4 |

It was observed that most of the mice had high titer neutralizing antibodies against Av1LacZ4 as a result of their previous exposure to an Adenovirus 5 based vector. Importantly, only 1 out of 15 samples had a detectable, although low, neutralization titer against Av12nBg. These results show that neutralizing antibodies against Adenovirus 5 are less effective in neutralizing the new virus, Av12nBg, with the chimeric hexon.

The disclosures of all patents, publications (including published patent applications), database accession numbers, and depository accession numbers referenced in this specification are specifically incorporated herein by reference in their entirety to the same extent as if each such individual patent, publication, database accession number, and depository accession number were specifically and individually indicated to be incorporated by reference.

It is to be understood, however, that the scope of the present invention is not to be limited to the specific embodiments described above. The invention may be practiced other than as particularly described and still be within the scope of the accompanying claims.

SEQUENCE LISTING (1) GENERAL INFORMATION:

(iii) NUMBER OF SEQUENCES:  7

(2) INFORMATION FOR SEQ ID NO: 1:

(i) SEQUENCE CHARACTERISTICS:
      (A) LENGTH:   29 bases
      (B) TYPE:     nucleic acid
      (C) STRANDEDNESS:  single
      (D) TOPOLOGY: linear (ii) MOLECULE TYPE:  polynucleotide (ix) FEATURE:
      (A) NAME/KEY: PCR primer (xi) SEQUENCE DESCRIPTION:     SEQ ID NO: 1:

GCGACCGGTC  GCAGCGTCTG  ACGCTGCGT                                       29

(2) INFORMATION FOR SEQ ID NO: 2:

(i) SEQUENCE CHARACTERISTICS:
      (A) LENGTH:   19 bases
      (B) TYPE:     nucleic acid
      (C) STRANDEDNESS:  single
      (D) TOPOLOGY: linear (ii) MOLECULE TYPE:  polynucleotide (ix) FEATURE:
            (A) NAME/KEY: PCR primer (xi) SEQUENCE DESCRIPTION:     SEQ ID NO: 2:

GTGAATGCGT ACCACGTCG                                                      19

(2) INFORMATION FOR SEQ ID NO: 3:

(i) SEQUENCE CHARACTERISTICS:
            (A) LENGTH:    31 bases
            (B) TYPE:      nucleic acid
            (C) STRANDEDNESS: single
            (D) TOPOLOGY: linear (ii) MOLECULE TYPE:  polynucleotide (ix) FEATURE:
            (A) NAME/KEY: PCR primer (xi) SEQUENCE DESCRIPTION:     SEQ ID NO: 3:

CGGTGTACAA CACAACTTGA GCAGTGTTTG C                                        31

(2) INFORMATION FOR SEQ ID NO: 4:

(i) SEQUENCE CHARACTERISTICS:
            (A) LENGTH:    919 amino acids
            (B) TYPE:      amino acid
            (C) STRANDEDNESS:
            (D) TOPOLOGY: linear (ii) MOLECULE TYPE:  protein (ix) FEATURE:
            (A) NAME/KEY: predicted hexon protein sequence
                for human Adenovirus 12

(xi) SEQUENCE DESCRIPTION:     SEQ ID NO: 4:

Met Ala Thr Pro Ser Met Met Pro Gln Trp
                  5                  10

Ser Tyr Met His Ile Ala Gly Gln Asp Ala
                 15                  20

Ser Glu Tyr Leu Ser Pro Gly Leu Val Gln
                 25                  30

Phe Ala Arg Ala Thr Asp Thr Tyr Phe Thr
                 35                  40

Leu Gly Asn Lys Phe Arg Asn Pro Thr Val
                 45                  50

Ala Pro Thr His Asp Val Thr Thr Asp Arg
                 55                  60

Ser Gln Arg Leu Thr Leu Arg Phe Val Pro
                 65                  70

Val Asp Arg Glu Asp Thr Thr Tyr Ser Tyr
                 75                  80

Lys Ala Arg Phe Thr Leu Ala Val Gly Asp
                 85                  90

Asn Arg Val Leu Asp Met Ala Ser Ser Tyr
                 95                 100

Phe Asp Ile Arg Gly Val Leu Asp Arg Gly
                105                 110

Pro Ser Phe Lys Pro Tyr Ser Gly Thr Ala
                115                 120

Tyr Asn Ser Leu Ala Pro Lys Gly Ala Pro

```
                        125                 130
Asn Ala Ser Glu Trp Ser Asp Asn Ala Lys
                    135                 140
Leu Asn Thr Phe Ala Gln Ala Pro Tyr Leu
                    145                 150
Ser Asp Thr Ile Thr Ala Ala Asp Gly Ile
                    155                 160
Lys Val Gly Thr Asp Thr Ala Gln Ala Gly
                    165                 170
Ala Ala Val Tyr Ala Asn Lys Thr Tyr Gln
                    175                 180
Pro Glu Pro Gln Val Gly Pro Ser Glu Trp
                    185                 190
Asn Thr Ser Ile Glu Asn Val Lys Ala Gly
                    195                 200
Gly Arg Ala Leu Lys Gln Thr Thr Ala Met
                    205                 210
Gln Pro Cys Tyr Gly Ser Tyr Ala Arg Pro
                    215                 220
Thr Asn Glu His Gly Gly Gln Ser Lys Asp
                    225                 230
Asp Asn Ile Glu Leu Lys Phe Phe Asp Ser
                    235                 240
Ala Asn Asn Ala Ala Asn Thr Ala Gln Val
                    245                 250
Val Phe Tyr Thr Glu Asp Val Asn Leu Glu
                    255                 260
Met Pro Asp Thr His Leu Val Phe Lys Pro
                    265                 270
Thr Val Thr Asn Gly Thr Ile Ala Ser Glu
                    275                 280
Ser Leu Leu Gly Gln Gln Ala Ala Pro Asn
                    285                 290
Arg Ala Asn Tyr Ile Ala Phe Arg Asp Asn
                    295                 300
Phe Ile Gly Leu Met Tyr Tyr Asn Ser Thr
                    305                 310
Gly Asn Met Gly Val Leu Ala Gly Gln Ala
                    315                 320
Ser Glu Leu Asn Ala Val Val Asp Leu Gln
                    325                 330
Asp Arg Asn Thr Glu Leu Ser Tyr Gln Leu
                    335                 340
Met Leu Asp Ala Leu Gly Asp Arg Thr Arg
                    345                 350
Tyr Phe Ser Leu Trp Asn Ser Ala Val Asp
                    355                 360
Ser Tyr Asp Pro Asp Val Arg Val Ile Glu
                    365                 370
Asn His Gly Val Glu Asp Glu Leu Pro Asn
                    375                 380
Tyr Cys Phe Pro Leu Ser Ala Val Gly Glu
                    385                 390
```

-continued

```
Ile Lys Asn Tyr Lys Gly Ile Lys Pro Asp
            395                 400

Asn Gly Gly Gly Gly Trp Thr Ala Asp
            405                 410

Asn Thr Val Ser Glu Ala Asn His Ile Gly
            415                 420

Ile Gly Asn Ile Ala Ala Met Glu Ile Asn
            425                 430

Leu Gln Ala Asn Leu Trp Arg Ser Phe Leu
            435                 440

Tyr Ser Asn Val Gly Leu Tyr Leu Pro Asp
            445                 450

Asp Leu Lys Tyr Thr Pro Gly Asn Ile Lys
            455                 460

Leu Pro Asp Asn Lys Asn Thr Tyr Glu Tyr
            465                 470

Met Asn Gly Arg Val Thr Ala Pro Gly Leu
            475                 480

Val Asp Thr Tyr Val Asn Ile Gly Ala Arg
            485                 490

Trp Ser Pro Asp Val Met Asp Asn Val Asn
            495                 500

Pro Phe Asn His His Arg Asn Ala Gly Leu
            505                 510

Arg Tyr Arg Ser Met Leu Leu Gly Asn Gly
            515                 520

Arg Phe Val Pro Phe His Ile Gln Val Pro
            525                 530

Gln Lys Phe Phe Ala Ile Arg Asn Leu Leu
            535                 540

Leu Leu Pro Gly Ser Tyr Thr Tyr Glu Trp
            545                 550

Asn Phe Arg Lys Asp Val Asn Met Ile Leu
            555                 560

Gln Ser Thr Leu Gly Asn Asp Leu Arg Val
            565                 570

Asp Gly Ala Ser Val Arg Phe Asp Asn Ile
            575                 580

Ala Leu Tyr Ala Asn Phe Phe Pro Met Ala
            585                 590

His Asn Thr Ala Ser Thr Leu Glu Ala Met
            595                 600

Leu Arg Asn Asp Thr Asn Asp Gln Ser Phe
            605                 610

Asn Asp Tyr Leu Cys Ala Ala Asn Met Leu
            615                 620

Tyr Pro Ile Pro Ala Asn Ala Thr Ser Val
            625                 630

Pro Ile Ser Ile Pro Ser Arg Asn Trp Ala
            635                 640

Ala Phe Arg Gly Trp Ser Phe Thr Arg Leu
            645                 650

Lys Thr Lys Glu Thr Pro Ser Leu Gly Ser
            655                 660
```

```
Gly Phe Asp Pro Tyr Phe Val Tyr Ser Gly
            665                 670

Thr Ile Pro Tyr Leu Asp Gly Thr Phe Tyr
            675                 680

Leu Asn His Thr Phe Lys Lys Val Ser Ile
            685                 690

Met Phe Asp Ser Ser Val Ser Trp Pro Gly
            695                 700

Asn Asp Arg Leu Leu Thr Pro Asn Glu Phe
            705                 710

Glu Ile Lys Arg Ser Val Asp Gly Glu Gly
            715                 720

Tyr Asn Val Ala Gln Cys Asn Met Thr Lys
            725                 730

Asp Trp Phe Leu Ile Gln Met Leu Ser His
            735                 740

Tyr Asn Ile Gly Tyr Gln Gly Phe Tyr Ile
            745                 750

Pro Glu Ser Tyr Lys Asp Arg Met Tyr Ser
            755                 760

Phe Phe Arg Asn Phe Gln Pro Met Ser Arg
            765                 770

Gln Val Val Asp Thr Thr Glu Tyr Lys Asn
            775                 780

Tyr Lys Lys Val Thr Val Glu Phe Gln His
            785                 790

Asn Asn Ser Gly Phe Val Gly Tyr Leu Gly
            795                 800

Pro Thr Met Arg Glu Gly Gln Ala Tyr Pro
            805                 810

Ala Asn Tyr Pro Tyr Pro Leu Ile Gly Gln
            815                 820

Thr Ala Val Glu Ser Ile Thr Gln Lys Lys
            825                 830

Phe Leu Cys Asp Arg Val Met Trp Arg Ile
            835                 840

Pro Phe Ser Ser Asn Phe Met Ser Met Gly
            845                 850

Ala Leu Thr Asp Leu Gly Gln Asn Met Leu
            855                 860

Tyr Ala Asn Ser Ala His Ala Leu Asp Met
            865                 870

Thr Phe Glu Val Asp Pro Met Asp Glu Pro
            875                 880

Thr Leu Leu Tyr Val Leu Phe Glu Val Phe
            885                 890

Asp Val Val Arg Ile His Gln Pro His Arg
            895                 900

Gly Val Ile Glu Ala Val Tyr Leu Arg Thr
            905                 910

Pro Phe Ser Ala Gly Asn Ala Thr Thr
            915
```

(2) INFORMATION FOR SEQ ID NO: 5:

(i) SEQUENCE CHARACTERISTICS:
        (A) LENGTH:    952 amino acids
        (B) TYPE:      amino acid
        (C) STRANDEDNESS:
        (D) TOPOLOGY: linear (ii) MOLECULE TYPE: protein (ix) FEATURE:
        (A) NAME/KEY: predicted hexon protein sequence
            for human Adenovirus 5

(xi) SEQUENCE DESCRIPTION:    SEQ ID NO: 5:

```
Met Ala Thr Pro Ser Met Met Pro Glu Trp
                 5                  10

Ser Tyr Met His Ile Ser Gly Gln Asp Ala
                15                  20

Ser Glu Tyr Leu Ser Pro Gly Leu Val Gln
                25                  30

Phe Ala Arg Ala Thr Glu Thr Tyr Phe Ser
                35                  40

Leu Asn Asn Lys Phe Arg Asn Pro Thr Val
                45                  50

Ala Pro Thr His Asp Val Thr Thr Asp Arg
                55                  60

Ser Gln Arg Leu Thr Leu Arg Phe Ile Pro
                65                  70

Val Asp Arg Glu Asp Thr Ala Tyr Ser Tyr
                75                  80

Lys Ala Arg Phe Thr Leu Ala Val Gly Asp
                85                  90

Asn Arg Val Leu Asp Met Ala Ser Thr Tyr
                95                 100

Phe Asp Ile Arg Gly Val Leu Asp Arg Gly
               105                 110

Pro Thr Phe Lys Pro Tyr Ser Gly Thr Ala
               115                 120

Tyr Asn Ala Leu Ala Pro Lys Gly Ala Pro
               125                 130

Asn Pro Cys Glu Trp Asp Glu Ala Ala Thr
               135                 140

Ala Leu Glu Ile Asn Leu Glu Glu Glu Asp
               145                 150

Asp Asp Asn Glu Asp Glu Val Asp Glu Gln
               155                 160

Ala Glu Gln Gln Lys Thr His Val Phe Gly
               165                 170

Gln Ala Pro Tyr Ser Gly Ile Asn Ile Thr
               175                 180

Lys Glu Gly Ile Gln Ile Gly Val Glu Gly
               185                 190

Gln Thr Pro Lys Tyr Ala Asp Lys Thr Phe
               195                 200

Gln Pro Glu Pro Gln Ile Gly Glu Ser Gln
               205                 210

Trp Tyr Glu Thr Glu Ile Asn His Ala Ala
```

```
                      215                 220
Gly Arg Val Leu Lys Lys Thr Thr Pro Met
                  225                 230
Lys Pro Cys Tyr Gly Ser Tyr Ala Lys Pro
                  235                 240
Thr Asn Glu Asn Gly Gly Gln Gly Ile Leu
                  245                 250
Val Lys Gln Gln Asn Gly Lys Leu Glu Ser
                  255                 260
Gln Val Glu Met Gln Phe Phe Ser Thr Thr
                  265                 270
Glu Ala Thr Ala Gly Asn Gly Asp Asn Leu
                  275                 280
Thr Pro Lys Val Val Leu Tyr Ser Glu Asp
                  285                 290
Val Asp Ile Glu Thr Pro Asp Thr His Ile
                  295                 300
Ser Tyr Met Pro Thr Ile Lys Glu Gly Asn
                  305                 310
Ser Arg Glu Leu Met Gly Gln Gln Ser Met
                  315                 320
Pro Asn Arg Pro Asn Tyr Ile Ala Phe Arg
                  325                 330
Asp Asn Phe Ile Gly Leu Met Tyr Tyr Asn
                  335                 340
Ser Thr Gly Asn Met Gly Val Leu Ala Gly
                  345                 350
Gln Ala Ser Gln Leu Asn Ala Val Val Asp
                  355                 360
Leu Gln Asp Arg Asn Thr Glu Leu Ser Tyr
                  365                 370
Gln Leu Leu Leu Asp Ser Ile Gly Asp Arg
                  375                 380
Thr Arg Tyr Phe Ser Met Trp Asn Gln Ala
                  385                 390
Val Asp Ser Tyr Asp Pro Asp Val Arg Ile
                  395                 400
Ile Glu Asn His Gly Thr Glu Asp Glu Leu
                  405                 410
Pro Asn Tyr Cys Phe Pro Leu Gly Gly Val
                  415                 420
Ile Asn Thr Glu Thr Leu Thr Lys Val Lys
                  425                 430
Pro Lys Thr Gly Gln Glu Asn Gly Trp Glu
                  435                 440
Lys Asp Ala Thr Glu Phe Ser Asp Lys Asn
                  445                 450
Glu Ile Arg Val Gly Asn Asn Phe Ala Met
                  455                 460
Glu Ile Asn Leu Asn Ala Asn Leu Trp Arg
                  465                 470
Asn Phe Leu Tyr Ser Asn Ile Ala Leu Tyr
                  475                 480
```

```
Leu Pro Asp Lys Leu Lys Tyr Ser Pro Ser
            485                 490

Asn Val Lys Ile Ser Asp Asn Pro Asn Thr
            495                 500

Tyr Asp Tyr Met Asn Lys Arg Val Val Ala
            505                 510

Pro Gly Leu Val Asp Cys Tyr Ile Asn Leu
            515                 520

Gly Ala Arg Trp Ser Leu Asp Tyr Met Asp
            525                 530

Asn Val Asn Pro Phe Asn His His Arg Asn
            535                 540

Ala Gly Leu Arg Tyr Arg Ser Met Leu Leu
            545                 550

Gly Asn Gly Arg Tyr Val Pro Phe His Ile
            555                 560

Gln Val Pro Gln Lys Phe Phe Ala Ile Lys
            565                 570

Asn Leu Leu Leu Leu Pro Gly Ser Tyr Thr
            575                 580

Tyr Glu Trp Asn Phe Arg Lys Asp Val Asn
            585                 590

Met Val Leu Gln Ser Ser Leu Gly Asn Asp
            595                 600

Leu Arg Val Asp Gly Ala Ser Ile Lys Phe
            605                 610

Asp Ser Ile Cys Leu Tyr Ala Thr Phe Phe
            615                 620

Pro Met Ala His Asn Thr Ala Ser Thr Leu
            625                 630

Glu Ala Met Leu Arg Asn Asp Thr Asn Asp
            635                 640

Gln Ser Phe Asn Asp Tyr Leu Ser Ala Ala
            645                 650

Asn Met Leu Tyr Pro Ile Pro Ala Asn Ala
            655                 660

Thr Asn Val Pro Ile Ser Ile Pro Ser Arg
            665                 670

Asn Trp Ala Ala Phe Arg Gly Trp Ala Phe
            675                 680

Thr Arg Leu Lys Thr Lys Glu Thr Pro Ser
            685                 690

Leu Gly Ser Gly Tyr Asp Pro Tyr Tyr Thr
            695                 700

Tyr Ser Gly Ser Ile Pro Tyr Leu Asp Gly
            705                 710

Thr Phe Tyr Leu Asn His Thr Phe Lys Lys
            715                 720

Val Ala Ile Thr Phe Asp Ser Ser Val Ser
            725                 730

Trp Pro Gly Asn Asp Arg Leu Leu Thr Pro
            735                 740

Asn Glu Phe Glu Ile Lys Arg Ser Val Asp
            745                 750
```

```
Gly Glu Gly Tyr Asn Val Ala Gln Cys Asn
            755                 760

Met Thr Lys Asp Trp Phe Leu Val Glu Met
            765                 770

Leu Ala Asn Tyr Asn Ile Gly Tyr Gln Gly
            775                 780

Phe Tyr Ile Pro Glu Ser Tyr Lys Asp Arg
            785                 790

Met Tyr Ser Phe Phe Arg Asn Phe Gln Pro
            795                 800

Met Ser Arg Gln Val Val Asp Asp Thr Lys
            805                 810

Tyr Lys Asp Tyr Gln Gln Val Gly Ile Leu
            815                 820

His Gln His Asn Asn Ser Gly Phe Val Gly
            825                 830

Tyr Leu Ala Pro Thr Met Arg Glu Gly Gln
            835                 840

Ala Tyr Pro Ala Asn Phe Pro Tyr Pro Leu
            845                 850

Ile Gly Lys Thr Ala Val Asp Ser Ile Thr
            855                 860

Gln Lys Lys Phe Leu Cys Asp Arg Thr Leu
            865                 870

Trp Arg Ile Pro Phe Ser Ser Asn Phe Met
            875                 880

Ser Met Gly Ala Leu Thr Asp Leu Gly Gln
            885                 890

Asn Leu Leu Tyr Ala Asn Ser Ala His Ala
            895                 900

Leu Asp Met Thr Phe Glu Val Asp Pro Met
            905                 910

Asp Glu Pro Thr Leu Leu Tyr Val Leu Phe
            915                 920

Glu Val Phe Asp Val Val Arg Val His Arg
            925                 930

Pro His Arg Gly Val Ile Glu Thr Val Tyr
            935                 940

Leu Arg Thr Pro Phe Ser Ala Gly Asn Ala
            945                 950

Thr Thr (2) INFORMATION FOR SEQ ID NO: 6:

(i) SEQUENCE CHARACTERISTICS:
        (A) LENGTH:   2760 bases
        (B) TYPE:     nucleic acid
        (C) STRANDEDNESS: single
        (D) TOPOLOGY: linear (ii) MOLECULE TYPE: polynucleotide (ix) FEATURE:
        (A) NAME/KEY: DNA sequence encoding hexon protein
            of Adenovirus 12

(xi) SEQUENCE DESCRIPTION:    SEQ ID NO: 6:
```

```
ATGGCCACTC CCTCGATGAT GCCGCAGTGG TCTTACATGC ACATCGCCGG TCAGGATGCC    60

TCGGAGTACC TGAGTCCCGG TCTGGTGCAA TTCGCCCGCG CCACGGACAC CTACTTCACC   120

CTGGAAACA AGTTTAGAAA CCCCACCGTG GCTCCCACCC ATGATGTTAC CACCGATCGC    180

TCGCAGCGTC TGACGCTGCG TTTTGTGCCC GTGGATCGGG AAGATACTAC CTACTCCTAC   240

AAGGCTCGCT TTACGCTGGC TGTGGGTGAC AACCGCGTGT TAGACATGGC TAGTTCTTAC   300

TTTGACATTC GAGGGTACT GGATCGTGGT CCCAGTTTTA AGCCCTATTC CGGAACCGCC    360

TACAATTCTT TGGCACCAAA AGGCGCTCCT AATGCTTCAC AATGGTCAGA TAACGCTAAG   420

CTTAATACCT TTGCTCAGGC GCCGTATCTT AGCGACACTA TCACCGCCGC CGATGGTATT   480

AAAGTTGGAA CAGACACCGC CCAGGCAGGC GCGGCGGTGT ATGCCAACAA AACTTATCAG   540

CCAGAGCCGC AAGTAGGACC AAGTGAATGG AACACCAGCA TTGAAAACGT TAAAGCTGGC   600

GGGAGGGCAT TAAAGCAAAC CACTGCAATG CAGCCGTGCT ATGGCTCCTA CGTCGTCCA    660

ACCAACGAAC ACGGAGGACA ATCCAAGGAT GACAACATTG AACTTAAGTT CTTTGATTCA   720

GCTAACAATG CAGCAAACAC TGCTCAAGTT GTGTTCTATA CCGAAGACGT AAACCTTGAA   780

ATGCCAGACA CGCATCTTGT GTTTAAGCCT ACTGTTACCA ATGGAACAAT TGCTTCTGAG   840

TCGCTGTTGG ACAGCAAGC AGCGCCAAAT AGAGCAAACT ACATTGCATT CAGAGATAAT    900

TTTATTGGCC TGATGTATTA CAACAGTACA GGCAACATGG GTGTATTGGC CGGGCAAGCT   960

TCCCAACTTA ACGCAGTAGT AGACCTGCAA GACAGAAATA CAGAGCTGTC ATACCAGTTA  1020

ATGCTGGATG CTTTGGGAGA CAGAACACGG TACTTTTCCT TGTGGAATTC CGCAGTGGAC  1080

AGTTACGACC CTGACGTTCG CGTTATTGAG AATCACGGGG TAGAGGATGA ACTACCAAAT  1140

TATTGCTTTC CTCTTAGCGC AGTAGGTGAA ATAAAAAATT ACAAAGGCAT TAAGCCAGAT  1200

AACGGAGGAG GAGGTGGCTG GACTGCCGAC AACACTGTCA GTGAAGCAAA CCACATAGGC  1260

ATTGGGAATA TAGCCGCCAT GGAAATTAAT TTGCAGGCTA ATTTGTGGAG AAGCTTCTTG  1320

TACTCAAATG TGGGCTTATA CCTACCAGAC GACTTAAAAT ACACTCCAGG AAACATAAAA  1380

CTACCTGATA ACAAGAACAC CTACGAGTAC ATGAACGGGC GTGTGACTGC CCCGGGGTTG  1440

GTGGATACCT ATGTCAATAT CGGCGCTCGC TGGTCCCCAG ATGTGATGGA TAATGTAAAC  1500

CCTTTTAACC ACCACCGAAA CGCAGGGTTG CGCTACAGAT CCATGTTGCT AGGCAATGGG  1560

AGATTTGTTC CTTTTCACAT TCAGGTGCCG CAAAAATTTT TTGCCATCAG AAATTTGTTG  1620

CTGTTGCCCG GTTCCTACAC TTACGAATGG AACTTTAGAA AGGATGTAAA CATGATTCTT  1680

CAGAGCACAC TGGGAAATGA TCTTCGGGTG GACGGAGCCA GCGTTCGCTT TGACAACATT  1740

GCCCTGTATG CTAACTTTTT TCCCATGGCA CATAACACAG CTTCTACTTT AGAAGCCATG  1800

TTAAGAAATG ACACCAACGA CCAGTCTTTT AACGATTATT TGTGTGCTGC AAACATGCTG  1860

TATCCCATCC CAGCTAACGC CACCAGCGTG CCCATTTCAA TACCTTCGCG AAATTGGGCG  1920

GCATTTAGAG GCTGGAGCTT TACTCGCCTA AAAACTAAAG AAACTCCTTC CCTGGGTTCA  1980

GGGTTTGACC CCTACTTTGT ATACTCTGGA ACCATTCCCT ATTTAGACGG CACCTTTTAC  2040

CTAAACCACA CTTTTAAGAA GGTGTCAATC ATGTTTGACT CCTCCGTGAG TTGGCCTGGA  2100

AATGACCGTT TGCTAACCCC AAATGAATTT GAAATAAAGC GTTCTGTGGA TGGGGAGGGA  2160

TACAATGTGG CCCAATGCAA TATGACTAAG GATTGGTTCC TAATACAAAT GCTTAGTCAT  2220

TACAACATTG GATACCAAGG TTTTTACATT CCAGAGAGCT ACAAGGACCG CATGTATTCT  2280

TTCTTTAGAA ACTTTCAGCC CATGAGTAGG CAAGTTGTGG ATACCACAGA ATATAAGAAC  2340

TACAAAAAAG TAACCGTAGA GTTTCAACAT AACAACTCAG GATTCGTGGG ATACCTGGGC  2400
```

-continued

| | |
|---|---|
| CCCACTATGC GGGAGGGACA AGCTTACCCC GCCAACTATC CCTACCCTCT TATAGGCCAA | 2460 |
| ACAGCTGTGG AAAGCATCAC ACAGAAAAAG TTTCTATGCG ATCGTGTTAT GTGGCGCATC | 2520 |
| CCATTTTCTA GTAACTTCAT GTCTATGGGG GCGCTAACGG ATCTTGGGCA AAATATGCTG | 2580 |
| TACGCAAACT CAGCCCATGC TCTAGACATG ACATTTGAGG TGGATCCAAT GGATGAGCCT | 2640 |
| ACCCTTCTTT ATGTTTTATT TGAAGTTTTC GACGTGGTAC GCATTCACCA GCCACACCGC | 2700 |
| GGCGTCATTG AAGCGGTCTA CCTGCGCACG CCCTTCTCGG CGGGTAACGC TACCACCTAA | 2760 |

(2) INFORMATION FOR SEQ ID NO: 7:

(i) SEQUENCE CHARACTERISTICS:
       (A) LENGTH: 2859 bases
       (B) TYPE: nucleic acid
       (C) STRANDEDNESS: single
       (D) TOPOLOGY: linear (ii) MOLECULE TYPE: polynucleotide (ix) FEATURE:
       (A) NAME/KEY: DNA sequence encoding hexon protein
          of Adenovirus 5.

(xi) SEQUENCE DESCRIPTION: SEQ ID NO: 7:

| | |
|---|---|
| ATGGCTACCC CTTCGATGAT GCCGCAGTGG TCTTACATGC ACATCTCGGG CCAGGACGCC | 60 |
| TCGGAGTACC TGAGCCCCGG GCTGGTGCAG TTTGCCCGCG CCACCGAGAC GTACTTCAGC | 120 |
| CTGAATAACA AGTTTAGAAA CCCCACGGTG GCGCCTACGC ACGACGTGAC CACAGACCGG | 180 |
| TCCCAGCGTT TGACGCTGCG GTTCATCCCT GTGGACCGTG AGGATACTGC GTACTCGTAC | 240 |
| AAGGCGCGGT TCACCCTAGC TGTGGGTGAT AACCGTGTGC TGGACATGGC TTCCACGTAC | 300 |
| TTTGACATCC GCGGCGTGCT GGACAGGGGC CCTACTTTTA AGCCCTACTC TGGCACTGCC | 360 |
| TACAACGCCC TGGCTCCCAA GGGTGCCCCA AATCCTTGCG AATGGGATGA AGCTGCTACT | 420 |
| GCTCTTGAAA TAAACCTAGA AGAAGAGGAC GATGACAACG AAGACGAAGT AGACGAGCAA | 480 |
| GCTGAGCAGC AAAAAACTCA CGTATTTGGG CAGGCGCCTT ATTCTGGTAT AAATATTACA | 540 |
| AAGGAGGGTA TTCAAATAGG TGTCGAAGGT CAAACACCTA AATATGCCGA TAAAACATTT | 600 |
| CAACCTGAAC CTCAAATAGG AGAATCTCAG TGGTACGAAA CTGAAATTAA TCATGCAGCT | 660 |
| GGGAGAGTCC TTAAAAAGAC TACCCCAATG AAACCATGTT ACGGTTCATA TGCAAAACCC | 720 |
| ACAAATGAAA ATGGAGGGCA AGGCATTCTT GTAAAGCAAC AAAATGGAAA GCTAGAAAGT | 780 |
| CAAGTGGAAA TGCAATTTTT CTCAACTACT GAGGCGACCG CAGGCAATGG TGATAACTTG | 840 |
| ACTCCTAAAG TGGTATTGTA CAGTGAAGAT GTAGATATAG AAACCCCAGA CACTCATATT | 900 |
| TCTTACATGC CCACTATTAA GGAAGGTAAC TCACGAGAAC TAATGGGCCA ACAATCTATG | 960 |
| CCCAACAGGC CTAATTACAT TGCTTTTAGG GACAATTTTA TTGGTCTAAT GTATTACAAC | 1020 |
| AGCACGGGTA ATATGGGTGT TCTGGCGGGC CAAGCATCGC AGTTGAATGC TGTTGTAGAT | 1080 |
| TTGCAAGACA GAAACACAGA GCTTTCATAC CAGCTTTTGC TTGATTCCAT TGGTGATAGA | 1140 |
| ACCAGGTACT TTTCTATGTG GAATCAGGCT GTTGACAGCT ATGATCCAGA TGTTAGAATT | 1200 |
| ATTGAAAATC ATGGAACTGA AGATGAACTT CCAAATTACT GCTTTCCACT GGGAGGTGTG | 1260 |
| ATTAATACAG AGACTCTTAC CAAGGTAAAA CCTAAAACAG GTCAGGAAAA TGGATGGGAA | 1320 |
| AAAGATGCTA CAGAATTTTC AGATAAAAAT GAAATAAGAG TTGGAAATAA TTTTGCCATG | 1380 |
| GAAATCAATC TAAATGCCAA CCTGTGGAGA AATTTCCTGT ACTCCAACAT AGCGCTGTAT | 1440 |
| TTGCCCGACA AGCTAAAGTA CAGTCCTTCC AACGTAAAAA TTTCTGATAA CCCAAACACC | 1500 |
| TACGACTACA TGAACAAGCG AGTGGTGGCT CCCGGGTTAG TGGACTGCTA CATTAACCTT | 1560 |

-continued

```
GGAGCACGCT GGTCCCTTGA CTATATGGAC AACGTCAACC CATTTAACCA CCACCGCAAT   1620

GCTGGCCTGC GCTACCGCTC AATGTTGCTG GGCAATGGTC GCTATGTGCC CTTCCACATC   1680

CAGGTGCCTC AGAAGTTCTT TGCCATTAAA AACCTCCTTC TCCTGCCGGG CTCATACACC   1740

TACGAGTGGA ACTTCAGGAA GGATGTTAAC ATGGTTCTGC AGAGCTCCCT AGGAAATGAC   1800

CTAAGGGTTG ACGGAGCCAG CATTAAGTTT GATAGCATTT GCCTTTACGC CACCTTCTTC   1860

CCCATGGCCC ACAACACCGC CTCCACGCTT GAGGCCATGC TTAGAAACGA CACCAACGAC   1920

CAGTCCTTTA ACGACTATCT CTCCGCCGCC AACATGCTCT ACCCTATACC CGCCAACGCT   1980

ACCAACGTGC CCATATCCAT CCCCTCCCGC AACTGGGCGG CTTTCCGCGG CTGGGCCTTC   2040

ACGCGCCTTA AGACTAAGGA AACCCCATCA CTGGGCTCGG GCTACGACCC TTATTACACC   2100

TACTCTGGCT CTATACCCTA CCTAGATGGA ACCTTTTACC TCAACCACAC CTTTAAGAAG   2160

GTGGCCATTA CCTTTGACTC TTCTGTCAGC TGGCCTGGCA ATGACCGCCT GCTTACCCCC   2220

AACGAGTTTG AAATTAAGCG CTCAGTTGAC GGGGAGGGTT ACAACGTTGC CCAGTGTAAC   2280

ATGACCAAAG ACTGGTTCCT GGTACAAATG CTAGCTAACT ACAACATTGG CTACCAGGGC   2340

TTCTATATCC CAGAGAGCTA CAAGGACCGC ATGTACTCCT TCTTTAGAAA CTTCCAGCCC   2400

ATGAGCCGTC AGGTGGTGGA TGATACTAAA TACAAGGACT ACCAACAGGT GGGCATCCTA   2460

CACCAACACA ACAACTCTGG ATTTGTTGGC TACCTTGCCC CCACCATGCG CGAAGGACAG   2520

GCCTACCCTG CTAACTTCCC CTATCCGCTT ATAGGCAAGA CCGCAGTTGA CAGCATTACC   2580

CAGAAAAAGT TTCTTTGCGA TCGCACCCTT TGGCGCATCC CATTCTCCAG TAACTTTATG   2640

TCCATGGGCG CACTCACAGA CCTGGGCCAA AACCTTCTCT ACGCCAACTC CGCCCACGCG   2700

CTAGACATGA CTTTTGAGGT GGATCCCATG GACGAGCCCA CCCTTCTTTA TGTTTTGTTT   2760

GAAGTCTTTG ACGTGGTCCG TGTGCACCGG CCGCACCGCG GCGTCATCGA AACCGTGTAC   2820

CTGCGCACGC CCTTCTCGGC CGGCAACGCC ACAACATAA                          2859
```

What is claimed is:

1. A modified adenovirus wherein said adenovirus, prior to modification, is of a first serotype, said first serotype being within a first subgenus, and, wherein, in the modified adenovirus at least a portion of at least one loop region of the hexon of said adenovirus is removed and replaced with at least a portion of at least one loop region of the hexon of an adenovirus of a second serotype, said second serotype being within a second subgenus.

2. The adenovirus of claim 1 wherein at least a portion of at least one of the L1 and L2 loop regions of the hexon of said adenovirus of said first serotype is removed and replaced with at least a portion of at least one of the L1 and L2 loop regions of the hexon of said adenovirus of said second serotype.

3. The adenovirus of claim 2 wherein at least a portion of each of the L1, L2, and L4 loop regions of the hexon of said adenovirus of said first serotype is removed and replaced with at least a portion of each of the L1, L2, and L4 loop regions of the hexon of said adenovirus of said second serotype.

4. The adenovirus of claim 3 wherein the L1, L2, and L4 loop regions of the hexon of said adenovirus of said first serotype are removed and replaced with the L1, L2, and L4 loop regions of the hexon of said adenovirus of said second serotype.

5. The adenovirus of claim 1 wherein said adenovirus of said first serotype is an adenovirus of a serotype within Subgenus C, and said adenovirus of said second serotype is an adenovirus of a serotype within a subgenus selected from the group consisting of Subgenera A, B, D, E, and F.

6. The adenovirus of claim 5 wherein said adenovirus of said second serotype is an adenovirus of a serotype within a subgenus selected from the group consisting of Subgenus A and Subgenus F.

7. The adenovirus of claim 5 wherein said adenovirus of said first serotype is selected from the group consisting of Adenovirus 2 and Adenovirus 5.

8. The adenovirus of claim 1 wherein said adenovirus of said first serotype is Adenovirus 5, and said adenovirus of said second serotype is Adenovirus 12.

9. The adenovirus of claim 1 wherein said adenovirus further includes at least one DNA sequence encoding a heterologous protein.

10. A method of expressing a heterologous protein in a host, comprising:

administering to a host the adenovirus of claim 9.

* * * * *